United States Patent
Raetz et al.

(10) Patent No.: US 6,465,631 B1
(45) Date of Patent: Oct. 15, 2002

(54) LIPID A 4' KINASE

(75) Inventors: Christian R. H. Raetz, Rougemont; Teresa A. Garrett, Durham, both of NC (US); Julie L. Kadrmas, Centerville, UT (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/080,205

(22) Filed: May 18, 1998

Related U.S. Application Data

(60) Provisional application No. 60/046,947, filed on May 19, 1997.

(51) Int. Cl.$^7$ ............................................. C07H 21/04
(52) U.S. Cl. ..................................... 536/23.2; 536/23.7
(58) Field of Search ........................ 435/6, 64.1, 252.3, 435/320.1, 325; 514/44; 536/23.2, 23.7, 24.32, 24.33

(56) References Cited

PUBLICATIONS

A. Kermouni et.al.; The IL–9 Receptor gene (IL9R): Genomic Structure, Chromosomal LOcalization in the Pseudoautosomal Region of the Long Arm of the Sex Chromosomes, and Identification of IL9R Pseudogenes at 9qter, 16pter, and 18pter, Genomics 29, 371–382.*
R. Ingalls et al.; Membrane Expression of Soluble Endotoxin–binding Proteins Permits Lipopolysaccharide Signaling in Chinese Hamster Ovary Fibroblasts Independently of CD14; May 1999, The Journal of Biological Chemistry, vol. 274, 13993–13998.*
S. Orkin et al.; Report and Recommendations of the Panel to Assess the NIH Investment in Research on Gene Therapy; 1995, Targeted Genetics, 1–38.*
W. Anderson; Human gene therapy; Apr. 1998 Nature, vol. 392. ; 25–30.*
I. Verma et.al.; Gene therapy– promises, problems and prospects, Sep. 1997, Nature vol. 389, 239–242.*
J. Rudinger; Characteristics of the amino acids as components of a peptide hormone sequence; Jun. 1976, Biological Council ,4–7.*
Gencore 4.5; U.S. 09–080–205–4, Nov. 2000.*
B. Alberts et.al.; Molecular Biology of The Cell; 441–444.*
C. Lam et.al; Immunostimulatory, but not Antiendotoxin, Activity of Lipid X is due to Small Amounts of Contaminating N, O–Acylated Disccharide–1–Phosphate: In Vitro and In Vivo Reevaluation of the Biological Activity of Synthetic Lipid X; Jul. 1991 Infecti.*
Ray et al, "The Biosynthesis of Gram–negative Endotoxin: A Novel Kinase In *Escherichia Coli* Membranes That Incorporates The 4'–Phosphate of Lipid A", The Journal of Biological Chemistry 202(3):1122–1128 (1987).
Hampton et al, "Lipid A 4'–Kinase form *Escherichia coli*: Enzyme Assay and Preparation of 4'–32P–Labeled Probes of High Specific Radioactivity", Methods in Enzymology 209:466–475 (1992).
Garrett et al, "Identification of the Gene Encoding the *Escherichia coli* Lipid A 4'–Kinase", The Journal of Biological Chemistry 272(35):2185521864 (1997).
Karow et al, "The essential *Escherichia coli* msbA gene, a multicopy suppressor of null mutations in the *htrB* gene, is related to the univesally conserved family of ATP–dependent translocators", Molecular Microbiology 7(1):69–79 (1993).

* cited by examiner

*Primary Examiner*—James Ketter
*Assistant Examiner*—Richard Schnizer
(74) *Attorney, Agent, or Firm*—Nixon & Vanderhye P.C.

(57) ABSTRACT

The present invention relates, in general, to lipid A 4' kinase and, in particular, to a nucleic acid encoding lipid A 4' kinase and to a method of producing lipid A 4' kinase recombinantly using same. The invention further relates to methods of producing 4' phosphorylated lipid A analogs using the recombinantly produced lipid A 4' kinase.

5 Claims, 18 Drawing Sheets

E. coli orfE DNA sequence

```
1    ATGATCGAAA AAATCTGGTC TGGTGAATCC CCTTTGTGGC GGCTATTGCT
51   GCCACTCTCC TGGTTGTATG GCCTGGTGAG TGGCGCGATC CGTCTTTGCT
101  ATAAACTAAA ACTGAAGCGC GCCTGGCGTG CCCCCGTACC GGTTGTCGTG
151  GTTGGTAATC TCACCGCAGG CGGCAACGGA AAACCCCGG TCGTTGTCTG
201  GCTGGTGGAA CAGTTGCAAC AGCGCGGTAT TCGCGTGGGG GTCGTATCGC
251  GGGGATATGG TGGTAAGGCT GAATCTTATC CGCTGTTATT GTCGGCAGAT
301  ACCACAACAG CACAGGCGGG TGATGAACCT GTGTTGATTT ATCAACGCAC
351  TGATGCGCCT GTTGCGGTTT CTCCCGTTCG TTCTGATGCG GTAAAAGCCA
401  TTCTGGCGCA ACACCCTGAT GTGCAGATCA TCGTAACCGA CGACGGTTTA
451  CAGCATTACC GTCTGGCGCG TGATGTGGAA ATTGTCGTTA TTGATGGTGT
501  GCGTCGCTTT GGCAATGGCT GGTGGTTGCC GGCGGGGCCA ATGCGTGAGC
551  GAGCGGGGCG CTTAAAGTCG GTTGATGCGG TAATCGTCAA CGGCGGTGTC
601  CCTCGCAGCG GTGAAATCCC CATGCATCTG CTGCCGGGTC AGGCGGTGAA
651  TTTACGTACC GGTACGCGTT GTGACGTTGC TCAGCTTGAA CATGTAGTGG
701  CGATGGCGGG GATTGGGCAT CCGCCGCGCT TTTTTGCCAC GCTGAAGATG
751  TGTGGCGTAC AACCGGAAAA ATGTGTACCG CTGGCCGATC ATCAGTCTTT
801  GAACCATGCG GATGTCAGTG CGTTGGTAAG CGCCGGGCAA ACGCTGGTAA
851  TGACTGAAAA AGATGCGGTG AAATGCCGGG CCTTTGCAGA AGAAAATTGG
901  TGGTATTTGC CTGTAGACGC ACAGCTTTCA GGTGATGAAC CAGCGAAACT
951  GCTTACGCAA CTAACCTTGC TGGCTTCTGG CAACTAG
```

Fig.1A

E. coli orfE amino acid sequence

```
1   MIEKIWSGES PLWRLLLPLS WLYGLVSGAI RLCYKLKLKR AWRAPVPVVV
51  VGNLTAGGNG KTPVVVWLVE QLQQRGIRVG VVSRGYGGKA ESYPLLLSAD
101 TTTAQAGDEP VLIYQRTDAP VAVSPVRSDA VKAILAQHPD VQIIVTDDGL
151 QHYRLARNVE IVVIDGVRRF GNGWWLPAGP MRERAGRLKS VDAVIVNGGV
201 PRSGEIPMHL LPGQAVNLRT GTRCDVAQLE HVVAMAGIGH PPRFFATLKM
251 CGVQPEKCVP LADHQSLNHA DVSALVSAGQ TLVMTEKDAV KCRAFAEENW
301 WYLPVDAQLS GDEPAKLLTQ LTLLASGN
```

Fig.1B

H. influenza orf DNA sequence

```
1    ATGCCCTTCT GGTATTCCAA CTCCAAACTT ATTTGGCTCT TATCGCCTTT
51   TTCTTTATTG TTTTGGTTGA TTAGCCAACT TCGTCGCGCC TTATTCTCTT
101  TGGGGCTGAA GTCTTCTTAT CGCGCACCAA AACCAGTGAT AATTGTGGGA
151  AATTTGTCTG TGGGTGGAAA TGGCAAAACG CCTGTGGTTG TTTGGCTTAT
201  GGAAGAATTA AAAAACGAG GTCTGCGTGT AGGTGTGATT TCTCGTGGTT
251  ACGGCAGTAA ATCTAAAACT TATCCGTTAT TCGTCACTAA AAATACAAAT
301  CCAATTGAAG GTGGCGATGA GCCTGTATTG ATCGCTAAAC GTACTAATGC
351  GCCAGTTGTG ATTTCCCCGA ATCGCCAGCA AGCGATTGAA TTACTCTTAA
401  GCCAAGCAGA GTGCGATATT ATTATTTCTG ATGATGGTTT GCAGCATTAT
451  CAATTACAAC GTGATTTAGA AATTGTCGTA ATGGACGCTG AGCGCGCATT
501  GGGAAATGGT TTTGTATTGC CAGCAGGTCC ATTGCGTGAA TTACCAAGTC
551  GATTAAAATC TGTCGATTTT GTGATCACTA ATGGTGGAAA AAATCAGTAT
601  TCAGATGCAG TTATGCGTCT TGTGCCTCAT TTCGCGATTA ATTTAAAAAC
651  CAATGAAAAA CGCCAATTAA ATGAATTTCA ATCTGGTGTT GCCATCGCAG
701  GGATTGGCAA TCCACAGCGT TTTTTTACTA TGTTAGAAAA GTTAGGGATT
751  CAGTTAAAGC AAACTCAAGC ATTTCAAGAT CATCAACATT TTGAAGCGTC
801  TCAATTAGAA AAACTTGCTG AAAATCAACC GCTCTTTATG ACGGAAAAAG
851  ATGCCGTAAA ATGCCAATCT TTTGCTAAAG ATAATTGGTG GTATGTCCCT
901  GTGGATGCGG AGATTATTGA GGCTGAAAAA CAACGTGAAA ATTTACCGCA
951  CTTTTGGGCC AAAATAGACA AACTTGTGGA GCAATACAGA AATGGC
```

Fig.2A

H. influenzae orf amino acid sequence

```
1   MPFWYSNSKL IWLLSPFSLL FWLISQLRRA LFSLGLKSSY RAPKPVIIVG
51  NLSVGGNGKT PVVVWLMEEL KKRGLRVGVI SRGYGSKSKT YPLFVTKNTN
101 PIEGGDEPVL IAKRTNAPVV ISPNRQQAIE LLLSQAECDI IISDDGLQHY
151 QLQRDLEIVV MDAERALGNG FVLPAGPLRE LPSRLKSVDF VITNGGKNQY
201 SDAVMRLVPH FAINLKTNEK RQLNEFQSGV AIAGIGNPQR FFTMLEKLGI
251 QLKQTQAFQD HQHFEASQLE KLAENQPLFM TEKDAVKCQS FAKDNWWYVP
301 VDAEIIEAEK QRENLPHFWA KIDKLVEQYR NG
```

Fig.2B

F. novicida valB DNA sequence

```
1    ATGCTAGATA AGATTTGGTA CAGATCAAAA CCAAACTTGC TTAGTCGGGT
51   GCTACAACCA ATATCTTTGG TTTTTATAGA TATTGCAAAT AAACGTAAAA
101  TAAAACAGCA ACTCAAGCAA TATAAATCAA AAATTCCTAT AATAGTTGTT
151  GGCAATATCT CTGTTGGCGG TACTGGCAAA ACTCCAGTTG TTAGAATGTT
201  GGCTCAGCAA TATTTAGCAC AAGGTAAAAA ACCAGCTATA ATTAGTCGTG
251  GATATGGTGC AAAGGCTGAT AATTATCCTT TTGAAGTAAC AAGTGGTACT
301  CTAGCAACTC AATGTGGCGA TGAGCCTGCG ATGTTATTTG ATGCTTTGCA
351  AGCACAGGTT CCTATTGTTA TTGCTCCAGA GAGAGTTCAG GCTGTTAAAT
401  ACATTGAAAA GAATTTTCCT GATACAGATA TAATTATATC TGATGATGGC
451  TTGCAACATT ATAAATTAGC TCGAGATAAG GAAATAGTGG TCGTAGATGC
501  TATTAGAATG TTTGGCAATA AATTATGTTT GCCTGCTGGT CCATTGAGAG
551  AACCGATTGA GAGATTAAAA GAAGTAGATC AAATTATAGT TATAGGTAAT
601  TGCTCAGATA AGATAAAGA GTTACTCAAA AACTATAAAA ATGTGACTTA
651  TGCAAAAGTC GTAGCTACTG AATTTGTTAA TATATTAACA GCTAAAAAAG
701  TAGCTAAGAC TGAATTTAAT CATCAAAATG TAATAGCTAT AGCAGGGATT
751  GGCAATCCAA CAAAATTTTT TAAGACTTTA GAAGAGAGTG CTATAAACAT
801  AACAGCTAAA AAAGTTTTTA AGATCACCA TAAGTTTACT CAGAGTGATT
851  TTGAGGGTAT AGATAGTGAC ATAACTGTAG TGATGACATA TAAAGATGCT
901  ATTAAATGCA AAAATTTTGC TAAAGCTAAT TGGTGGTATC TGGATATAGC
951  TTTAGATATC AATGTTTAA
```

Fig.3A

F. novicida valB amino acid sequence

```
1    MLDKIWYRSK PNLLSRVLQP ISLVFIDIAN KRKIKQQLKQ YKSKIPIIVV
51   GNISVGGTGK TPVVRMLAQQ YLAQGKKPAI ISRGYGAKAD NYPFEVTSGT
101  LATQCGDEPA MLFDALQAQV PIVIAPERVQ AVKYIEKNFP DTDIIISDDG
151  LQHYKLARDK EIVVVDAIRM FGNKLCLPAG PLREPIERLK EVDQIIVIGN
201  CSDKDKELLK NYKNVTYAKV VATEFVNILT AKKVAKTEFN HQNVIAIAGI
251  GNPTKFFKTL EESAINITAK KVFKDHHKFT QSDFEGIDSD ITVVMTYKDA
301  IKCKNFAKAN WWYLDIALDI NV
```

Fig.3B

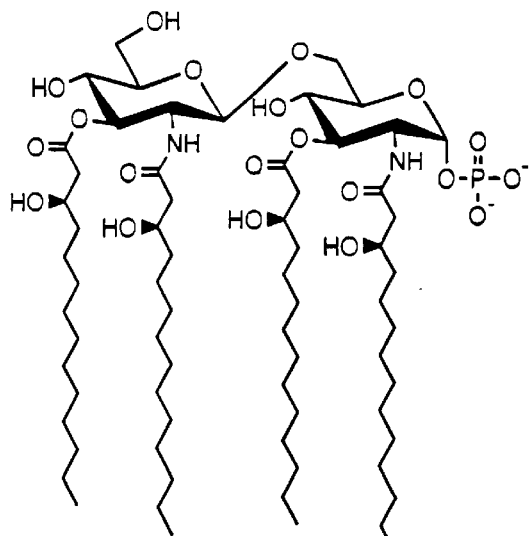 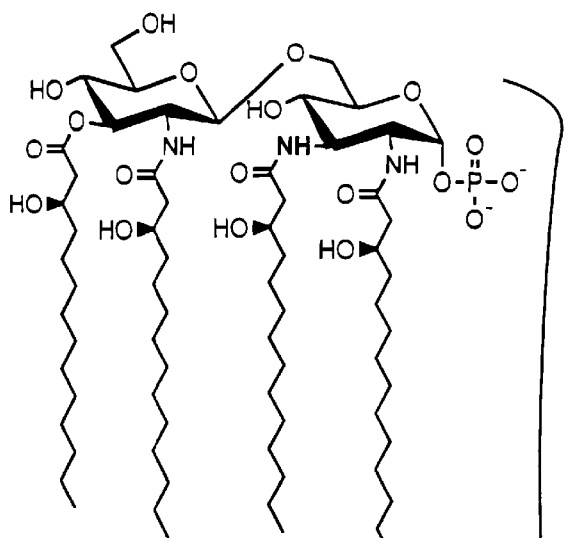
DS-1-P  3-aza-DS-1-P
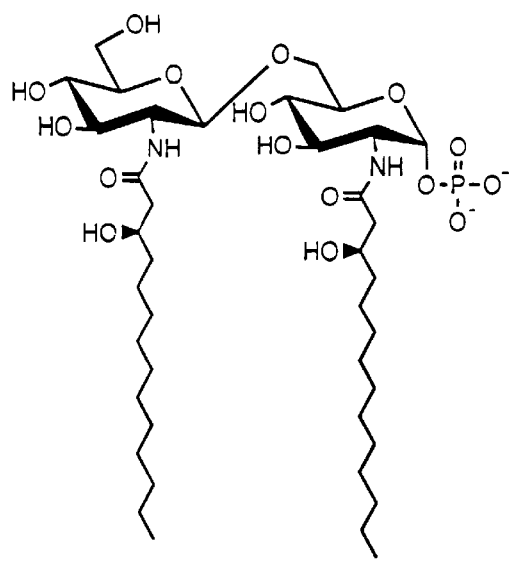 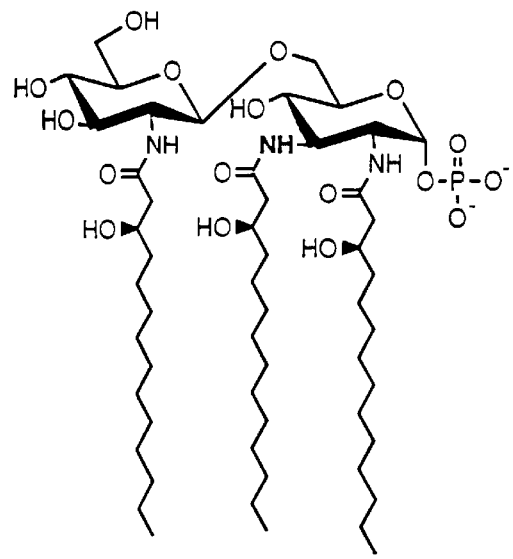
Base-treated DS-1-P  Base-treated 3-aza-DS-1-P
Fig.11

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 1
gtttggcata tgatcgaaaa aatctgg                                      27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 2
attcatggat ccatcaatcg aacgctg                                      27

<210> SEQ ID NO 3
<211> LENGTH: 987
<212> TYPE: DNA
<213> ORGANISM: Escherichia coli

<400> SEQUENCE: 3
atgatcgaaa aaatctggtc tggtgaatcc cctttgtggc ggctattgct gccactctcc    60
tggttgtatg gcctggtgag tggcgcgatc cgtctttgct ataaactaaa actgaagcgc   120
gcctggcgtg cccccgtacc ggttgtcgtg gttggtaatc tcaccgcagg cggcaacgga   180
aaacccccgg tcgttgtctg gctggtggaa cagttgcaac agcgcggtat tcgcgtgggg   240
gtcgtatcgc ggggatatgg tggtaaggct gaatcttatc cgctgttatt gtcggcagat   300
accacaacag cacaggcggg tgatgaacct gtgttgattt atcaacgcac tgatgcgcct   360
gttgcggttt ctcccgttcg ttctgatgcg gtaaaagcca ttctggcgca cacccctgat   420
gtgcagatca tcgtaaccga cgacggttta cagcattacc gtctggcgcg tgatgtggaa   480
attgtcgtta ttgatggtgt gcgtcgcttt ggcaatggct ggtggttgcc ggcggggcca   540
atgcgtgagc gagcggggcg cttaaagtcg gttgatgcgg taatcgtcaa cggcggtgtc   600
cctcgcagcg gtgaaatccc catgcatctg ctgccgggtc aggcggtgaa tttacgtacc   660
ggtacgcgtt gtgacgttgc tcagcttgaa catgtagtgg cgatggcggg gattgggcat   720
ccgccgcgct ttttgccac gctgaagatg tgtggcgtac aaccggaaaa atgtgtaccg   780
ctggccgatc atcagtcttt gaaccatgcg gatgtcagtg cgttggtaag cgccgggcaa   840
acgctggtaa tgactgaaaa agatgcggtg aaatgccggg cctttgcaga agaaaattgg   900
tggtatttgc ctgtagacgc acagctttca ggtgatgaac cagcgaaact gcttacgcaa   960
ctaaccttgc tggcttctgg caactag                                      987

<210> SEQ ID NO 4
<211> LENGTH: 328
<212> TYPE: PRT
<213> ORGANISM: Escherichia coli

<400> SEQUENCE: 4

Met Ile Glu Lys Ile Trp Ser Gly Glu Ser Pro Leu Trp Arg Leu Leu

|  1 |  | 5 |  |  |  | 10 |  |  |  | 15 |  |
|---|---|---|---|---|---|---|---|---|---|---|---|

Leu Pro Leu Ser Trp Leu Tyr Gly Leu Val Ser Gly Ala Ile Arg Leu
                20                  25                  30

Cys Tyr Lys Leu Lys Leu Lys Arg Ala Trp Arg Ala Pro Val Pro Val
                35                  40                  45

Val Val Val Gly Asn Leu Thr Ala Gly Gly Asn Gly Lys Thr Pro Val
            50                  55                  60

Val Val Trp Leu Val Glu Gln Leu Gln Gln Arg Gly Ile Arg Val Gly
65                  70                  75                  80

Val Val Ser Arg Gly Tyr Gly Lys Ala Glu Ser Tyr Pro Leu Leu
                    85                  90                  95

Leu Ser Ala Asp Thr Thr Thr Ala Gln Ala Gly Asp Glu Pro Val Leu
                100                 105                 110

Ile Tyr Gln Arg Thr Asp Ala Pro Val Ala Val Ser Pro Val Arg Ser
                115                 120                 125

Asp Ala Val Lys Ala Ile Leu Ala Gln His Pro Asp Val Gln Ile Ile
    130                 135                 140

Val Thr Asp Asp Gly Leu Gln His Tyr Arg Leu Ala Arg Asp Val Glu
145                 150                 155                 160

Ile Val Val Ile Asp Gly Val Arg Arg Phe Gly Asn Gly Trp Trp Leu
                165                 170                 175

Pro Ala Gly Pro Met Arg Glu Arg Ala Gly Arg Leu Lys Ser Val Asp
                180                 185                 190

Ala Val Ile Val Asn Gly Gly Val Pro Arg Ser Gly Glu Ile Pro Met
                195                 200                 205

His Leu Leu Pro Gly Gln Ala Val Asn Leu Arg Thr Gly Thr Arg Cys
    210                 215                 220

Asp Val Ala Gln Leu Glu His Val Val Ala Met Ala Gly Ile Gly His
225                 230                 235                 240

Pro Pro Arg Phe Phe Ala Thr Leu Lys Met Cys Gly Val Gln Pro Glu
                245                 250                 255

Lys Cys Val Pro Leu Ala Asp His Gln Ser Leu Asn His Ala Asp Val
                260                 265                 270

Ser Ala Leu Val Ser Ala Gly Gln Thr Leu Val Met Thr Glu Lys Asp
                275                 280                 285

Ala Val Lys Cys Arg Ala Phe Ala Glu Glu Asn Trp Trp Tyr Leu Pro
    290                 295                 300

Val Asp Ala Gln Leu Ser Gly Asp Glu Pro Ala Lys Leu Leu Thr Gln
305                 310                 315                 320

Leu Thr Leu Leu Ala Ser Gly Asn
                325

<210> SEQ ID NO 5
<211> LENGTH: 996
<212> TYPE: DNA
<213> ORGANISM: Haemophilus influenzae

<400> SEQUENCE: 5

```
atgcccttct ggtattccaa ctccaaactt atttggctct tatcgccttt ttctttattg    60
ttttggttga ttagccaact tcgtcgcgcc ttattctctt tggggctgaa gtcttcttat   120
cgcgcaccaa aaccagtgat aattgtggga aatttgtctg tgggtggaaa tggcaaaacg   180
cctgtggttg tttggcttat ggaagaatta aaaaaacgag gtctgcgtgt aggtgtgatt   240
tctcgtggtt acggcagtaa atctaaaact tatccgttat cgtcactaa aaatacaaat    300
```

```
ccaattgaag gtggcgatga gcctgtattg atcgctaaac gtactaatgc gccagttgtg    360
atttccccga atcgccagca agcgattgaa ttactcttaa gccaagcaga gtgcgatatt    420
attatttctg atgatggttt gcagcattat caattacaac gtgatttaga aattgtcgta    480
atggacgctg agcgcgcatt gggaaatggt tttgtattgc cagcaggtcc attgcgtgaa    540
ttaccaagtc gattaaaatc tgtcgatttt gtgatcacta atggtggaaa aaatcagtat    600
tcagatgcag ttatgcgtct tgtgcctcat ttcgcgatta atttaaaaac caatgaaaaa    660
cgccaattaa atgaatttca atctggtgtt gccatcgcag ggattggcaa tccacagcgt    720
ttttttacta tgttagaaaa gttagggatt cagttaaagc aaactcaagc atttcaagat    780
catcaacatt ttgaagcgtc tcaattagaa aaacttgctg aaaatcaacc gctctttatg    840
acggaaaaag atgccgtaaa atgccaatct tttgctaaag ataattggtg gtatgtccct    900
gtggatgcgg agattattga ggctgaaaaa caacgtgaaa atttaccgca ctttggggcc    960
aaaatagaca aacttgtgga gcaatacaga aatggc                              996
```

```
<210> SEQ ID NO 6
<211> LENGTH: 332
<212> TYPE: PRT
<213> ORGANISM: Haemophilus influenzae

<400> SEQUENCE: 6
```

```
Met Pro Phe Trp Tyr Ser Asn Ser Lys Leu Ile Trp Leu Leu Ser Pro
  1               5                  10                  15

Phe Ser Leu Leu Phe Trp Leu Ile Ser Gln Leu Arg Arg Ala Leu Phe
             20                  25                  30

Ser Leu Gly Leu Lys Ser Ser Tyr Arg Ala Pro Lys Pro Val Ile Ile
         35                  40                  45

Val Gly Asn Leu Ser Val Gly Gly Asn Gly Lys Thr Pro Val Val Val
     50                  55                  60

Trp Leu Met Glu Glu Leu Lys Lys Arg Gly Leu Arg Val Gly Val Ile
 65                  70                  75                  80

Ser Arg Gly Tyr Gly Ser Lys Ser Lys Thr Tyr Pro Leu Phe Val Thr
                 85                  90                  95

Lys Asn Thr Asn Pro Ile Glu Gly Gly Asp Glu Pro Val Leu Ile Ala
            100                 105                 110

Lys Arg Thr Asn Ala Pro Val Val Ile Ser Pro Asn Arg Gln Gln Ala
        115                 120                 125

Ile Glu Leu Leu Leu Ser Gln Ala Glu Cys Asp Ile Ile Ser Asp
    130                 135                 140

Asp Gly Leu Gln His Tyr Gln Leu Gln Arg Asp Leu Glu Ile Val Val
145                 150                 155                 160

Met Asp Ala Glu Arg Ala Leu Gly Asn Gly Phe Val Leu Pro Ala Gly
                165                 170                 175

Pro Leu Arg Glu Leu Pro Ser Arg Leu Lys Ser Val Asp Phe Val Ile
            180                 185                 190

Thr Asn Gly Gly Lys Asn Gln Tyr Ser Asp Ala Val Met Arg Leu Val
        195                 200                 205

Pro His Phe Ala Ile Asn Leu Lys Thr Asn Glu Lys Arg Gln Leu Asn
    210                 215                 220

Glu Phe Gln Ser Gly Val Ala Ile Ala Gly Ile Gly Asn Pro Gln Arg
225                 230                 235                 240

Phe Phe Thr Met Leu Glu Lys Leu Gly Ile Gln Leu Lys Gln Thr Gln
```

```
                      245                  250                      255
    Ala Phe Gln Asp His Gln His Phe Glu Ala Ser Gln Leu Glu Lys Leu
                            260                  265                  270

Ala Glu Asn Gln Pro Leu Phe Met Thr Glu Lys Asp Ala Val Lys Cys
                275                      280                  285

Gln Ser Phe Ala Lys Asp Asn Trp Trp Tyr Val Pro Val Asp Ala Glu
                290                  295                  300

Ile Ile Glu Ala Glu Lys Gln Arg Glu Asn Leu Pro His Phe Trp Ala
    305                 310                  315                  320

Lys Ile Asp Lys Leu Val Glu Gln Tyr Arg Asn Gly
                    325                  330
```

<210> SEQ ID NO 7
<211> LENGTH: 969
<212> TYPE: DNA
<213> ORGANISM: Francisella novcida

<400> SEQUENCE: 7

```
atgctagata agatttggta cagatcaaaa ccaaacttgc ttagtcgggt gctacaacca    60
atatctttgg ttttatagaa tattgcaaat aaacgtaaaa taaacagca actcaagcaa   120
tataaatcaa aaattcctat aatagttgtt ggcaatatct ctgttggcgg tactggcaaa   180
actccagttg ttagaatgtt ggctcagcaa tatttagcac aaggtaaaaa accagctata   240
attagtcgtg gatatggtgc aaaggctgat aattatcctt ttgaagtaac aagtggtact   300
ctagcaactc aatgtggcga tgagcctgcg atgttatttg atgctttgca agcacaggtt   360
cctattgtta ttgctccaga gagagttcag gctgttaaat acattgaaaa gaattttcct   420
gatacagata taattatatc tgatgatggc ttgcaacatt ataaattagc tcgagataag   480
gaaatagtgg tcgtagatgc tattagaatg tttggcaata aattatgttt gcctgctggt   540
ccattgagag aaccgattga gagattaaaa gaagtagatc aaattatagt tataggtaat   600
tgctcagata agataaaga gttactcaaa actataaaaa atgtgactta tgcaaaagtc   660
gtagctactg aatttgttaa tatattaaca gctaaaaaag tagctaagac tgaatttaat   720
catcaaaatg taatagctat agcagggatt ggcaatccaa caaaatttttt taagacttta   780
gaagagagtg ctataaacat aacagctaaa aaagttttta agatcacca taagttttact   840
cagagtgatt ttgagggtat agatagtgac ataactgtag tgatgacata taagatgct   900
attaaatgca aaaattttgc taaagctaat tggtggtatc tggatatagc tttagatatc   960
aatgttttaa                                                          969
```

<210> SEQ ID NO 8
<211> LENGTH: 322
<212> TYPE: PRT
<213> ORGANISM: Francisella novcida

<400> SEQUENCE: 8

```
Met Leu Asp Lys Ile Trp Tyr Arg Ser Lys Pro Asn Leu Leu Ser Arg
  1               5                  10                  15

Val Leu Gln Pro Ile Ser Leu Val Phe Ile Asp Ile Ala Asn Lys Arg
                20                  25                  30

Lys Ile Lys Gln Gln Leu Lys Gln Tyr Lys Ser Lys Ile Pro Ile Ile
            35                  40                  45

Val Val Gly Asn Ile Ser Val Gly Gly Thr Gly Lys Thr Pro Val Val
        50                  55                  60
```

-continued

```
Arg Met Leu Ala Gln Gln Tyr Leu Ala Gln Gly Lys Lys Pro Ala Ile
 65                  70                  75                  80

Ile Ser Arg Gly Tyr Gly Ala Lys Ala Asp Asn Tyr Pro Phe Glu Val
                 85                  90                  95

Thr Ser Gly Thr Leu Ala Thr Gln Cys Gly Asp Glu Pro Ala Met Leu
            100                 105                 110

Phe Asp Ala Leu Gln Ala Gln Val Pro Ile Val Ile Ala Pro Glu Arg
        115                 120                 125

Val Gln Ala Val Lys Tyr Ile Glu Lys Asn Phe Pro Asp Thr Asp Ile
    130                 135                 140

Ile Ile Ser Asp Asp Gly Leu Gln His Tyr Lys Leu Ala Arg Asp Lys
145                 150                 155                 160

Glu Ile Val Val Asp Ala Ile Arg Met Phe Gly Asn Lys Leu Cys
                165                 170                 175

Leu Pro Ala Gly Pro Leu Arg Glu Pro Ile Glu Arg Leu Lys Glu Val
            180                 185                 190

Asp Gln Ile Ile Val Ile Gly Asn Cys Ser Asp Lys Asp Lys Glu Leu
        195                 200                 205

Leu Lys Asn Tyr Lys Asn Val Thr Tyr Ala Lys Val Val Ala Thr Glu
    210                 215                 220

Phe Val Asn Ile Leu Thr Ala Lys Lys Val Ala Lys Thr Glu Phe Asn
225                 230                 235                 240

His Gln Asn Val Ile Ala Ile Ala Gly Ile Gly Asn Pro Thr Lys Phe
                245                 250                 255

Phe Lys Thr Leu Glu Glu Ser Ala Ile Asn Ile Thr Ala Lys Lys Val
            260                 265                 270

Phe Lys Asp His His Lys Phe Thr Gln Ser Asp Phe Glu Gly Ile Asp
        275                 280                 285

Ser Asp Ile Thr Val Val Met Thr Tyr Lys Asp Ala Ile Lys Cys Lys
    290                 295                 300

Asn Phe Ala Lys Ala Asn Trp Trp Tyr Leu Asp Ile Ala Leu Asp Ile
305                 310                 315                 320

Asn Val
```

LIPID A 4' KINASE

This application claims benefit of priority to provisional appplicaiton No. 60/046,947, filed May 19, 1997.

This application was made with Government support under Grant Nos. 5RO1 GM51310 and 5RO1 GM51796 awarded by the National Institutes of Health and Grant No. DBE092-53851 awarded by the National Science Foundation. The Government has certain rights in the invention.

TECHNICAL FIELD

The present invention relates, in general, to lipid A 4' kinase and, in particular, to a nucleic acid encoding lipid A 4' kinase and to a method of producing lipid A 4' kinase recombinantly using same. The invention further relates to methods of producing 4' phosphorylated lipid A analogs using the recombinantly produced lipid A 4' kinase.

BACKGROUND

Lipopolysaccharide (LPS) is the major glycolipid of the outer membrane of gram-negative bacteria. Lipid A, or endotoxin, is the hydrophobic anchor of LPS, and it is a potent immunostimulant. It appears to be responsible for many of the features of septic shock that can accompany severe gram-negative infections. Lipid A is a disaccharide of glucosamine that is phosphorylated at the 1 and 4' positions and is acylated with R-3 hydroxymyristate at the 2, 3, 2', and 3' positions. In E. coli, two additional fatty acyl chains are also esterified to the 2' and 3' R-3 hydroxymyristate groups to form acyloxyacyl units.

Lipid A biosynthesis begins with the acyl-ACP dependent acylation of UDP-N-acetylglucosamine (Anderson et al, J. Biol. Chem. 260:15536 (1985), Anderson et al, J. Biol. Chem. 262:5159 (1987), Anderson et al, J. Biol. Chem. 268:19858 (1993), Williamson et al, J. Bacteriol. 173:3591 (1991), Raetz et al, Science 270:997 (1995)). Nine enzymes are required for the complete synthesis of $Kdo_2$-lipid A (Raetz, J. Bacteriol. 175:5745 (1993), Raetz, Escherichia coli and Salmonella: Cellular and Molecular Biology (Neidhardt, F. C., ed) Vol. 1, Second Ed., pp. 1035–1063, American Society for Microbiology, Washington, D.C. (1996), Raetz et al, J. Biol. Chem. 265:1235 (1990)). Seven of the nine structural genes coding for the enzymes of lipid A biosynthesis in E. coli have been identified, however, the lipid A 4' kinase gene has remained elusive (Raetz, Escherichia coli and Salmonella: Cellular and Molecular Biology (Neidhardt, F. C., ed) Vol. 1, Second Ed., pp. 1035–1063, American Society for Microbiology, Washington, D.C. (1996)). The 4' kinase catalyzes the sixth step of the pathway (FIG. 2) (Ray et al, J. Biol. Chem. 262:1122 (1987)). It phosphorylates the 4' position of a tetraacyldisaccharide-1-phosphate intermediate (termed DS-1-P) to form tetraacyldisaccharide 1, 4' bis-phosphate, also known as lipid IVA (FIG. 2) (Ray et al, J. Biol. Chem. 262:1122 (1987), Raetz et al, J. Biol. Chem. 260:16080 (1985), Strain et al, J. Biol. Chem. 260:16089 (1985)).

Identification of the 4' kinase gene has been hampered because mutants lacking the 4' kinase have not been identified (Raetz, Escherichia coli and Salmonella: Cellular and Molecular Biology (Neidhardt, F. C., ed) Vol. 1, Second Ed., pp. 1035–1063, American Society for Microbiology, Washington, D.C. (1996)). Attempts to purify the kinase to homogeneity have been thwarted by the protein's association with membranes and its instability in the presence of detergents (Ray et al, J. Biol. Chem. 262:1122 (1987), Hampton et al, Methods in Enzymology 209:466 (1992)).

The lipid A 4' kinase can be used to make $4'-{}^{32}P$ labeled lipid A precursors, such as $[4'-{}^{32}P]$-lipid IVA and $Kdo_2$-$[4'-{}^{32}P]$-lipid IVA, for biochemical analyses of late pathway reactions. The 4' kinase activity found in wild type E. coli membranes, however, is relatively inefficient and unstable, especially in the presence of low chemical concentrations of ATP. The inability to achieve high levels of ${}^{32}P$ transfer makes it virtually impossible to use the 4' kinase for phosphorylating DS-1-P analogs that are utilized less rapidly. Identification and overexpression of the 4' kinase gene would facilitate the synthesis of 4' phosphorylated lipid A analogs with activity as endotoxin antagonists or mimetics (Raetz, J. Bacteriol. 175:5745 (1993), Raetz, Escherichia coli and Salmonella: Cellular and Molecular Biology (Neidhardt, F. C., ed) Vol. 1, Second Ed., pp. 1035–1063, American Society for Microbiology, Washington, D.C. (1996)). The present invention provides a nucleic acid encoding lipid A 4' kinase and a method of producing 4' kinase using same.

OBJECTS AND SUMMARY OF THE INVENTION

It is a general object of the invention to provide a nucleic acid encoding lipid A 4' kinase.

It is another object of the invention to provide a method of producing lipid A 4' kinase recombinantly.

It is a further object of the invention to provide a recombinantly produced lipid A 4' kinase.

It is a further object of the invention to provide a method of producing lipid A analogs suitable for use as endotoxin mimetics or endotoxin antagonists, using lipid A 4' kinase.

The foregoing objects are met by the present invention which relates to a nucleic acid encoding 4' kinase, to an expression construct comprising that nucleic acid and to a host cell into which the construct has been introduced. The invention further relates to a method of producing 4' kinase using such host cells and to the 4' kinase produced thereby. In addition, the invention relates to the production of 4' phosphorylated lipid A analogs using the recombinantly produced 4' kinase.

Further objects and advantages of the invention will be clear from the description that follows.

BRIEF DESCRIPTION OF THE DRAWINGS

FIGS. 1A and B: (A) is a DNA sequence encoding E. coli lipid A 4' kinase orfE (SEQ ID NO:3) and (B) is the encoded amino acid sequence (SEQ ID NO:4) (see also Karow et al, Mol. Microbiol. 7:69 (1993)).

FIGS. 2A and B: (A) is a DNA sequence encoding Haemophilus influenzae, orfE (SEQ ID NO:5) and (B) is the encoded amino acid sequence (SEQ ID NO:6).

FIGS. 3A and B: (A) is a DNA sequence encoding Francisella novcida orfE (SEQ ID NO:7) and (B) is the encoded amino acid sequence (SEQ ID NO:8).

FIG. 11: Chemical structure of DS-1-P analogs tested as 4' kinase substrates. The chemical structures of DS-1-P and three analogs are shown. The 3-aza-DS-1-P has an amide linked hydroxymyristate group at the 3 position instead of an ester linked group (relevant NH indicated in bold). Mild base hydrolysis of these compounds results in removal of the ester linked hydroxymyristate groups. The resulting compounds, base-treated DS-1-P and base-treated 3-aza-DS-1-P, are also shown.

DETAILED DESCRIPTION OF THE INVENTION

Figure 4:
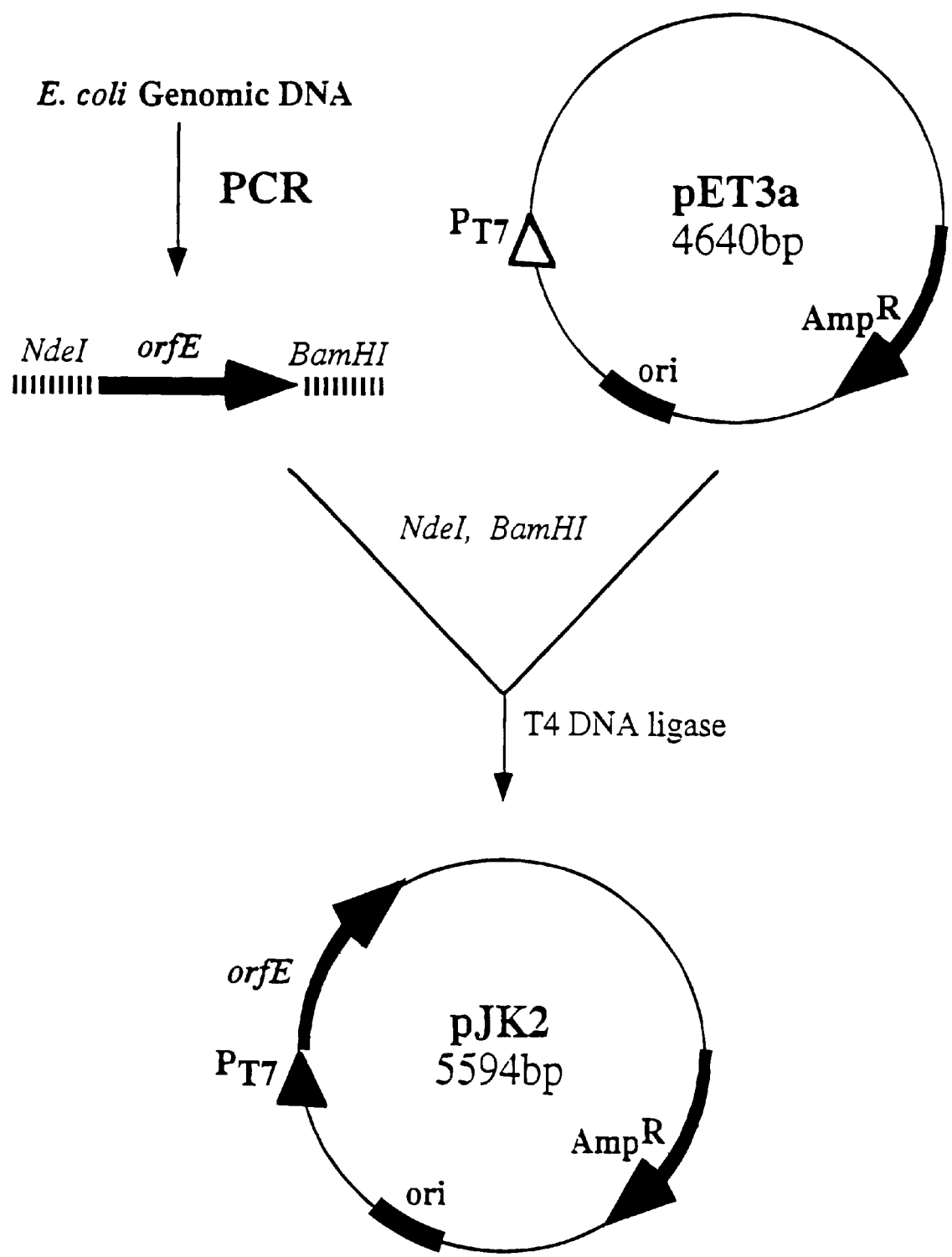
FIG. 4: Construction of pJK2.

The present invention relates to lipid A 4' kinase and to a nucleic acid sequence encoding same (see for example, FIG. 1A and B). The invention further relates to a method of preparing 4' phosphorylated lipid A analogs with activity as endotoxin mimetics or antagonists.

In one embodiment, the invention relates to gram-negative bacterial lipid A 4' kinase, for example, E. coli 4' kinase. In a specific embodiment, the 4' kinase has the amino acid sequence shown in FIG. 1B or an allelic variation thereof (eg a naturally occurring allelic variant) or a variant of the FIG. 1B sequence from a bacterial species other than E. coli. The variant sequences retain the functional characteristics of the FIG. 1B sequence. Variant sequences can be identified using a complementation assay such as that described in Examples that follow. Examples of variant sequences include the protein encoded in an open reading frame identified in the Haemophilus influenzae Rd genome (Fleischmann et al, Science 269:496 (1995) (see FIGS. 2A and B) and the protein encoded in the valB gene (Mdluli et al, Microbiology 140:3309 (1994)) from *Francisella novicida* (see FIGS. 3A and B).

The present invention relates not only to the entirety of the 4' kinase protein, for example, the FIG. 1B sequence or variations thereof as defined above, but to portions thereof as well. The term "portions" relates to peptides and polypeptides of at least 6 or at least 10 amino acids in length, preferably, at least 25, at least 50, at least 100 or at least 300 amino acids. One such portion is an N-terminal truncated form (eg truncated to remove the putative transmembrane domain) of 4' kinase (eg the FIG 1B sequence from which amino acids 1–70 have been removed).

In addition to the 4' kinase protein, the present invention also relates to a nucleic acid sequence (DNA or RNA) encoding the 4' kinase, eg gram-negative bacterial 4' kinase, and to fragments thereof suitable for use, for example, as probes or primers, of at least 18, preferably at least 30, more preferably at least 75, 150, 300, or 900 bases in length, that encode the "portions" described above. In a specific embodiment, the invention relates to a nucleic acid sequence encoding the FIG. 1B amino acid sequence, or portion or variant thereof as defined above. In particular, the present invention relates to the FIG. 1A nucleic acid sequence or fragments thereof. The nucleic acid can be present in isolated form, for example, free of nucleic acids with which it is normally associated (eg free of the msbA encoding sequence in the case of the FIG. 1A sequence). The present invention also relates to a nucleic acid sequence substantially identical to the nucleic acid sequence of FIG. 1A. A "substantially identical" sequence is one the complement of which hybridizes to the nucleic acid sequence of FIG. 1A. An example of stringency conditions that can be used to identify "substantially identical" sequences by Southern hybridization is as follows: hybridization at 42° C. for 24 hours in 20% formamide, 5×SSC (1× is 0.15 M NaCl, 0.015 M NaCitrate), 5×Denhardt's solution, 1% SDS, 150 μg/ml salmon sperm DNA, and 1.5×10$^6$ cpm/ml $^{32}$P random primed lpxK probe; two washes are carried out using 2×SSC, 0.1% SDS @ 42° C., once with same buffer for 10 minutes at room temperature. (See Hyland et al, J. Bacteriology 179:2029 (1997)). (For details of reagent preparation, etc, see Sambrook et al, Molecular Cloning, A Laboratory Manual, 2nd Edition). The invention also relates to nucleic acids complementary to those described above.

The present invention also relates to a recombinant molecule (a construct) comprising a nucleic acid sequence as described above and to a host cell transformed therewith. Using methodologies well known in the art, a recombinant molecule comprising a vector and a nucleic acid sequence encoding a 4' kinase of the invention, or portion or variant thereof as defined above, can be constructed. Vectors suitable for use in the present invention include plasmid and viral vectors (for example, lambda, pET, pUC18 or 19, pACYC 184, pT7, pING (procayotic vectors) and, pcDNA 1, 2 or 3, adenovirus, adeno-associated virus, retrovirus (eucaryotic vectors)). Appropriate vectors can be selected based on their compatibility with transformation into a selected host cell. The nucleotide sequence of the invention can be present in the vector operably linked to regulatory elements, for example, a promoter. Suitable promoters include, but are not limited to the T7, lac, tac, ara, CMV and SV40 promoters. Preferably, the nucleic acid of FIG. 1A is not operably linked (via msbA) to the msbA promoter.

As indicated above, the recombinant molecule of the invention can be constructed so as to be suitable for transforming a host cell. Suitable host cells include prokaryotic cells, such as bacteria, particularly gram negative bacteria such as E. coli. Gram positve bacteria are also suitable hosts, as are eucaryotic cells such as yeast and insect cells. The recombinant molecule of the invention can be introduced into appropriate host cells using a variety of known methods.

The present invention further relates to a method of producing the 4' kinase of the invention, or portion or variant thereof as defined above. The method comprises culturing the above-described transformed host cells under conditions such that the encoding sequence is expressed and the protein thereby produced. The protein can be isolated as described in the Examples that follow. The protein can be further purified using standard procedures, advantageously, in the presence of a non-ionic detergent (such as Triton X100). (See, for example, Belunis and Raetz, J. Biol. Chem. 267:9988 (1992).)

The 4' kinase of the invention, or portion or variant thereof as defined above, can be present in isolated form, for example, substantially free of proteins with which it is normally associated. Quantitative Western blotting as described by Pardridge et al (J. Biol. Chem. 265:18035 (1990)) can be used to determine the ratio of lipid A 4' kinase present relative to, for example, Msb. Advantageously, the protein is at least 5% pure, as determined, for example, by gel electrophoresis. The proteins, polypeptides and peptides of the invention can be produced recombinantly using the nucleic acid sequences as described above, or chemically using known methods. When prepared recombinantly, the protein of the invention can be produced alone or as a fusion product, for example, fused with a protein such as the maltose binding protein, glutathione-S-transferase or β-galactosidase. For example, the coding sequence of the invention (eg the sequence encoding the E. coli 4' kinase) can be cloned in frame with a sequence encoding another protein (such as those referenced above) and the fusion product expressed in an appropriate host cell. The coding sequence of the invention can also be expressed as a C- or N-terminal histidine or epitope tagged product in order to facilitate purification (a C-terminal histidine tagged product (for example, tagged with 6 histidine residues) retains activity).

The proteins, polypeptides and peptides of the invention can be used as antigens to generate 4' kinase specific antibodies, particularly, antibodies specific for E. coli 4' kinase. Methods of antibody generation are well known in the art. Both monoclonal and polyclonal antibodies are contemplated, as are antigen binding fragments thereof. Such antibodies can be used, for example to, effect purification of the protein using, for instance, affinity chromatography.

The 4' kinase of the invention, present either in purified form or in a lysate of a cell in which it has been overexpressed, can be used to produce lipid A analogs that are phosphorylated. In the case of disaccharides, phosphorylation at the 4' is preferred. In certain substrate analogs, phosphorylation can occur at other available hydroxyl groups. Lipid A analogs with the greatest potency (either as endotoxin mimetics or endotoxin antagonists) are those that are phosphorylated both at positions 1 and 4' (Golenbock et al, J. Biol. Chem. 266:19490 (1991) and references cited therein; Raetz, *Escherichia coli* and Salmonella: Cellular and Molecular Biology (Neidhardt, F. C., ed) Vol. 1, Second Ed., pp. 1035–1063, American Society for Microbiology, Washington, D.C. (1996), Golenbock et al, J. Biol. Chem. 266:19490 (1991), Christ et al, J. Am. Chem. Soc. 116:3637 (1994), Christ et al, Science 265:80 (1995), Takayama et al, Infect. Immun. 57:1336 (1989)). Examples of lipid A-like molecules suitable as substrates for the 4' kinase of the invention include disaccharides (eg 2 glucosamines) with preferably 2–7 (more preferably 4–6) acyl (preferably a $C_2$–$C_{20}$ acyl, more preferably a $C_{10}$–$C_{16}$ acyl) or alkyl (preferably, a $C_2$–$C_{20}$ alkyl, more preferably a $C_{10}$–$C_{16}$ alkyl) chains. Lipid A-like molecules that display either endotoxin agonist or antagonist activity can contain 5 or 6 acyl (or alkyl) chains (see also suitable substrates described in DE 3834876, DE 3834877 and WO 8700174). Advantageously, a phosphate is present at the 1 position of the substrate and —OH at the 4' position. The phosphate donor used in the reactions can be unlabelled or labeled, for example, radiolabelled, or labelled with a heavy isotope such as ($^{18}$O).

Endotoxin antagonists produced in accordance with the invention can be used for treating complications of gram-negative sepsis as well the diseases/disorders enumerated in U.S. Pat. No. 4,918,061. The endotoxin mimetics produced in accordance with the invention can be used as adjuvants or as immunostimulants.

Immunostimulation of a patient can be effected using the lipid A 4' kinase encoding sequence of the invention. The lipid A 4' kinase encoding sequence can, for example, be introduced into macrophages (or other immune cell types (eg dendritic cells or stem cells)) under conditions such that the encoding sequence is expressed. The lipid A 4' kinase encoding sequence can be introduced, for example, using a vector, eg a viral (eg a retroviral, adenoviral or adeno-associated viral) vector. The immune cells can be transfected with the lipid A 4' kinase sequence ex vivo and subsequently (re)introduced into the patient. Immunostimulation is can be effected by administering to the patient a precursor of lipid A agonist (eg a substrate of lipid A 4' kinase that, upon 4' phosphorylation, is activated to a lipid A agonist). Activation of the precursor by the expression product of the lipid A 4' kinase encoding sequence results in immunostimulation. Various precursors can be used and optimum transfection and dosing regimens can be established by one skilled in the art without undue experimentation. Candidates for immunostimulation as described above include immunodeficient or otherwise compromised patients (eg HIV patents and cancer patients). The immunostimulatory approach described can be used alone or in combination with other therapies (eg anti-infective therapies), depending on the effect sought.

Certain aspects of the present invention are described in greater detail in the non-limiting Examples that follow.

EXAMPLES

The following experimental details are relevant to the specific Examples that follow.

Bacterial strains and growth conditions. Table I lists the strains used. Cells were cultured at 37° in Luria Broth (LB) consisting of 5 g of NaCl, 5 g of yeast extract, and 10 g tryptone/liter (Miller, Exp. Mol. Genet., Cold Spring Harbor Lab. Cold Spring Harbor, N.Y. (1972)). Antibiotics were added, when required, at 50 μg/ml for ampicillin, 12 μg/ml for tetracycline and 30 μg/ml for chloramphenicol.

TABLE I

Plasmids and *E. coli* strains used in this study

| Strain or plasmid | Relevant genotype | Reference |
| --- | --- | --- |
| W3110 | Wild-type, F-, λ- | CGSC, Yale University |
| BR7 | dgk-6-zjb-729::Tn10, ΔuncBC | (55) |
| BLR(DE3)pLysS | cm', tet' | Novagen |
| pET3a | vector, amp' | Novagen |
| pJK2 | pET 3a containing orfE coding region | This Work |

DNA techniques. *E. coli* chromosomal DNA was isolated as described by Ausbel et al, Current Prot. Mol. Biol., John Wiley & Sons, N.Y. (1989). Mini preparations of plasmid DNA were made using the Promega Wizard mini purification system. Large scale preparations of plasmid DNA were made using the 5'-3' Bigger Prep kit. PCR reactions were optimized using the Stratagene Optiprime Kit. DNA fragments were isolated from agarose gels using the Qiagen Qiaex 11 gel extraction kit.

Restriction enzymes and T4 ligase were used according to the manufacturer's directions. Transformation of *E. coli* with plasmid DNAs was done using salt competent cells (Maniatis et al, Mol. Cloning: A Lab. Manual, Cold Spring Harbor, Cold Spring Harbor, N.Y. (1982)).

Lipid substrates. DS-1-$^{32}$P was made according to Radika et al, (J. Biol. Chem. 263:14859 (1988)). Milligram quantities DS-1-P were enzymatically synthesized from UDP-2, 3-diacyl-glucosamine and 2,3-diacyl-glucosamine-1-phosphate (lipid X) using a partially purified *E. coli* disaccharide synthase preparation (Radika et al, J. Biol. Chem. 263:14859 (1988)). 3-aza-DS-1-P was made in the same manner except that 3-aza-lipid X (Haselberger et al, Triangle 26:33 (1987)) was used in place of lipid X. Base-treated DS-1-P was made by treating 2 mg of DS-1-P for 30 minutes with 0.2 M NaOH in 1 ml chloroform:methanol (2:1, v/v). The mixture was diluted 10 fold with chloroform-:methanol (95:5) and loaded onto a 5 ml silica column equilibrated with 50 ml chloroform:methanol (95:5). The column was washed with 25 ml of each of the following ratios (v/v) of chloroform:methanol: 95:5, 90:10, 70:30, 1:1, 30:70 and 20:80. Thirty 5 ml fractions were collected. The resolved hydroxy fatty acids and the deacylated DS-1-P were detected by spotting 5 µl of each fraction onto a thin layer chromatography plate, developing the plate in chloroform:methanol:water:acetic acid (25:15:4:2, v/v), and charring with sulfuric acid. The hydroxy fatty acid eluted with the 70:30 v/v solvent mixture. The base-treated, deacylated DS-1-P eluted with the 1:1 solvent ratio. The relevant fractions were pooled, and the solvent removed by rotary evaporation. The base-treated, deacylated 3-aza-DS-1-P was prepared in the same manner. The elution profile for this compound was the same as for the base-treated, deacylated DS-1-P. For use as substrates in 4' kinase assays, all lipid substrates were dispersed in 50 mM Hepes, pH 7.4, by sonic irradiation for 2 minutes.

Kohara λ library preparation and screen for 4' kinase activity. Fresh lysates of the Kohara λ library were made following the method of Clementz et al with slight modifications (J. Biol. Chem. 271:12095 (1996)). The host $E.\ coli$ strain, W3110, was grown overnight at 37° C. in LB medium, supplemented with 0.2% maltose and 10 mM $MgSO_4$. The culture was diluted 1:1 with 10 mM $CaCl_2$, 10 mM $MgCl_2$. The λ lysates used by Clementz et al (J. Biol. Chem. 271:12095 (1996)), were diluted 1:100 and 1:100 in SM buffer (5.8 g NaCl, 2 g $MgSO_4$, 50 ml 1 M Tris, pH 7.5 per liter). Using 96-well microtiter plates, 5 µl of the individual diluted lysates and 10 µl of the diluted host cell suspension were mixed and incubated at 37° C. for 15 minutes. LB medium supplemented with 10 mM $MgSO_4$ (150 µl) was added to each well and incubation continued at 37° C. After 4 hours, the $OD_{600}$ of each well was measured using a Molecular Dynamics Spectramax 250 microplate reader. When the cell suspension had cleared to an $OD_{600}$ less than 0.1, it was considered lysed, and was transferred to a fresh microtiter plate at 4° C. Lysis was evaluated every hour until 8 hours after infection. The lysates originating from the 1:1000 dilution of the originals were chosen for assay. Any hybrid λ bacteriophages that did not yield fresh suitable lysates with the 1:1000 dilutions of the original stock were generally obtained from the 1:100 dilutions of the original stock. The final lysates were stored at −80° C. overnight. The 4' kinase activity of each lysate was assayed in a 10 µl reaction mixture containing 5 µl of lysate, 100 µM DS-1-$^{32}$P (1000 cpm/nmol), 1 mg/ml cardiolipin, 50 mM Tris, pH 8.5, 5 mM ATP, 1% NP-40, and 5 mM $MgCl_2$. After incubation at 30° C. for 60 minutes, the reaction was stopped by spotting 5 µl onto a Silica Gel 60 TLC plate. The plates were developed in chloroform:methanol:water:acetic acid (25:15:4:2, v/v), dried, and exposed to a Molecular Dynamics PhosphorImager screen. Conversion of DS-1-$^{32}$P to [1-$^{32}$P]-lipid $IV_A$ was quantified using ImageQuant software (Molecular Dynamics).

Construction of pJK2 bearing orfE under the control of a T7 promoter. The gene encoded by the open reading frame orfE was cloned into pET3a cloning vector (Novagen). orfE was amplified by PCR of $E.\ coli$ genomic DNA using pfu DNA polymerase (according to manufacturer's specification) and the following primers: 5'GTTTG-GCATATGATCGAAAAAATCTGG 3' (SEQ ID NO:1) and 5'ATTCATGGATCCATCAATCGAACGCTG 3' (SEQ ID NO:2). The first primer introduces a Nde I site at the start codon of orfE, and the second primer introduces a BamHl site downstream of the stop codon. The PCR product was digested with Nde I and BamHl, and ligated into a similarly cut pET3a vector. A portion of the ligation reaction was transformed into $E.\ coli$ SURE cells (Stratagene, La Jolla, Calif.), and colonies resistant to ampicillin were selected. Plasmid DNA was isolated from ampicillin resistant clones and was digested with BamHl and Ndel to identify those constructs that contained the desired 1 kb insert. This plasmid is called pJK2 (see FIG. 4).

Expression of the orfE gene product: pJK2 was transformed into BLR(DE3)pLysS cells and grown at 37° C. in 2 liters of LB. When the cultures reached an $A_{600}$ of 0.6, IPTG was added (final concentration of 1 mM) to induce expression of the orfE gene product. After 3 hours of induction, the cells were collected by centrifugation at 10,000×g for 15 minutes at 4° C., washed with 1 liter of 50 mM Hepes, pH 7.5, and resuspended in 30 ml of the wash buffer. Cells were broken in a cold french pressure cell at 20,000 psi, and unbroken cells were removed by centrifugation at 3,500× g to form the cell-free extract. The membrane and soluble fractions were isolated by centrifugation of the entire cell-free extract at 150,000×g for 60 minutes. After centrifugation, the soluble fraction was removed to a fresh tube, and the membrane pellet resuspended in 50 ml 50 mM Hepes, pH 7.5. The soluble fraction and the resuspended membranes were both centrifuged a second time. The final membrane pellet was resuspended by homogenization in 10 ml of the Hepes buffer and stored frozen in aliquots at −80° C. The membrane free cytosol was also stored in aliquots at −80° C. The protein concentration was determined using the BioRad protein assay kit with bovine serum albumin as a standard.

Assays for 4' kinase activity. Two methods for analyzing 4' kinase activity of various protein fractions were employed. The first (method I) utilizes DS-1-$^{32}$P as the labeled substrate. Typically, 100 µM DS-1-$^{32}$P (1000 cpm/nmol), 1 mg/ml cardiolipin, 50 mM Tris, pH 8.5, 5 mM ATP, 1% NP-40, and 5 mM $MgCl_2$ are mixed with 0.5–500 µg/ml protein fraction and incubated at 30° C. for various times. Reactions were stopped by spotting a portion of the reaction onto a Silica Gel 60 thin layer chromatography plate. Plates were developed in chloroform:methanol:water:acetic acid (25:15:4:2, v/v) and analyzed as described above. Method II (which is not intended for the quantitative determination of specific activities) utilizes [γ-$^{32}$P] ATP (~8×10$^6$ cpm/nmol) as the labeled substrate. The reaction conditions are exactly the same as for method I except that the ATP concentration is lowered to 0.6 µM and only non-radioactive DS-1-P (final concentration of 100 µM) is added. The reactions were stopped as described above, and plates were developed in chloroform:pyridine:formic acid:water (30:70:16:10, v/v).

Example I

Screening for Overproduction of Lipid A 4' Kinase in Kohara Library λ Lysates

Kohara et al (Cell 50:495 (1987)) have generated a library of 3400 mapped hybrid λ, bacteriophage clones which cover the $E.\ coli$ genome. A subset of this library containing 476 λ clones is available which covers 99% of the genome with some overlap between the clones (Clementz et al, J. Biol. Chem. 271:12095 (1996), Borodovsky et al, Trends Biochem. Sci. 19:309 (1994)). Clementz et al showed that enzymatic activity could be detected in $E.\ coli$ lysates produced by these hybrid λ clones. Activities of several enzymes involved in LPS biosynthesis were detected, and lysates generated from the λ clones containing the gene coding for the enzymes of interest displayed 5 to 10 fold overproduction of the activities.

The same approach was employed to identify the gene for the lipid A 4' kinase. The 4' kinase activity was assayed in the lysates using method I (DS-1-$^{32}$P and 5 mM ATP). Under these conditions, product formation was linear with respect to time and protein concentration, there were no side products, and the results were reproducible for a given lysate.

Figure 6:
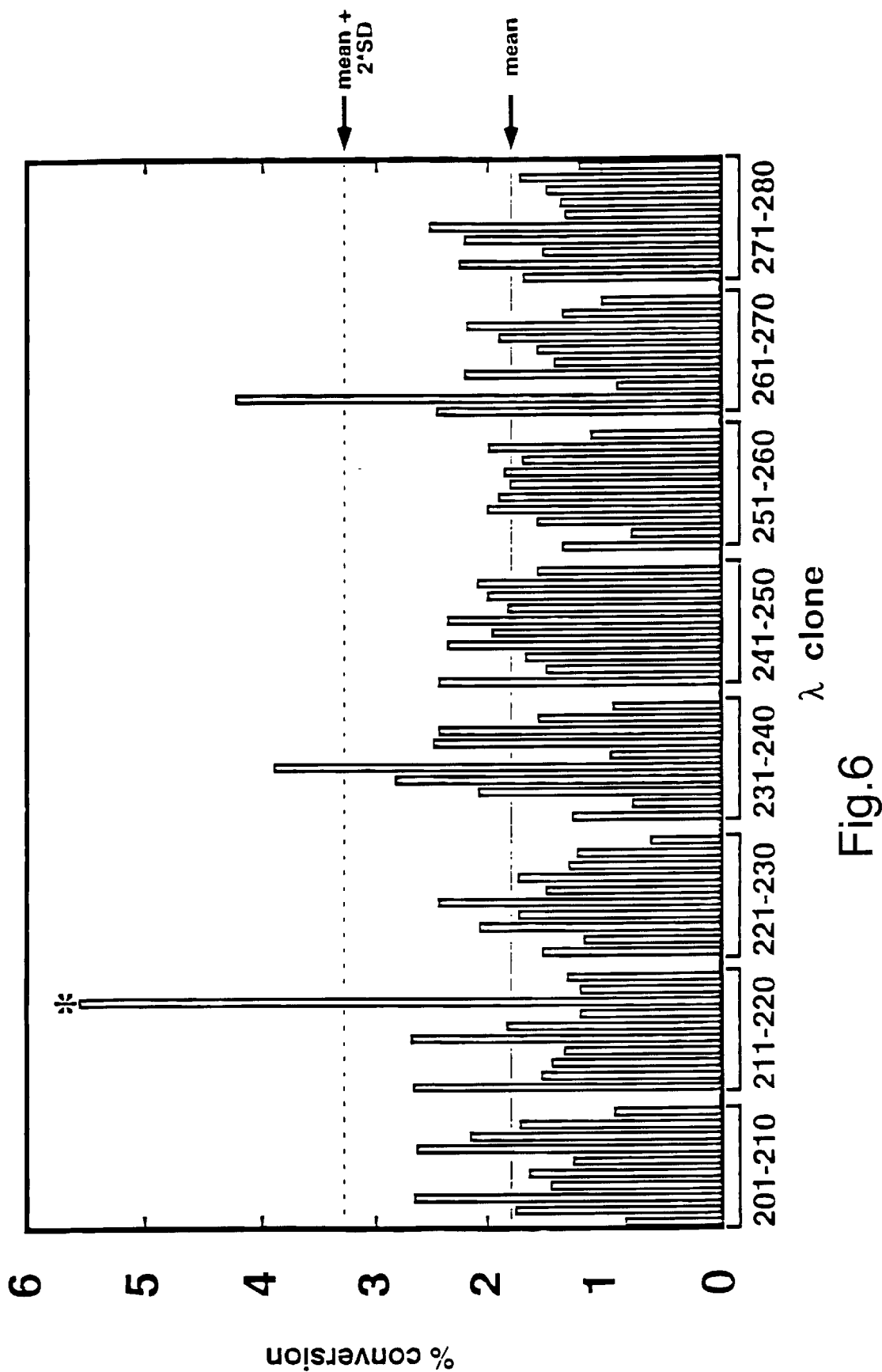
FIG. 6: Assays of E. coli lysates generated with individual hybrid λ bacteriophages [201]4H7 to [280]22E3 for 4' kinase activity. The λ bacteriophages [201]4H7 to [280] 22E3 represent one sixth of the Kohara miniset library (Kohara et al, Cell 50:495 (1987), Borodovsky et al, Trends Biochem. Sci. 19:309 (1994)). The 4' kinase activity was assayed in a 10 μl reaction mixture containing 100 μM DS-1-$^{32}$P (1000 cpm/nmol), 1 mg/ml cardiolipin, 50 mM Tris, pH 8.5, 5 mM ATP, 5 mM MgCl$_2$, 1% NP-40, and 5 μl of lysate. After 60 minutes at 30° C., the reaction was stopped by spotting 5 μl onto a Silica Gel 60 TLC plate. The plates were developed in chloroform:methanol:water:acetic acid (25:15:4:2, v/v). After chromatography, the plate was dried under a cold air stream, exposed to a PhosphorImager screen, and visualized using ImageQuant software (Molecular Dynamics). The histogram shows the % conversion of DS-1-$^{32}$P to [1-$^{32}$P]-lipid IV$_A$ for 80 of the 476 lysates tested. The asterisk highlights λ clone [218]E1D1. The mean and standard deviation for the 80 lysates of this set were determined. The solid line shows the mean value, and the dashed line shows the mean plus two standard deviations. Any lysates showing activity above the dashed line were re-assayed.

Fresh λ lysates of W3110 were prepared and assayed for 4' kinase activity in 6 sets of 80. FIG. 6 shows the assay results for one set, hybrid λ clones [201]4H7 to [280]22E3. No single lysate in the collection gave the 5 to 10 fold overproduction seen with other enzymes of lipid A biosynthesis. However, there were several lysates with significantly higher activity than their neighboring lysates (FIG. 6). In order to choose lysates for further analysis, the mean and standard deviation for each set of 80 was calculated. Fifteen clones, the activity of which surpassed the mean by more than two standard deviations, were reassayed. One lysate, [218]E1D1 (marked by bold asterisk in FIG. 6) consistently displayed 2–2.5 fold more kinase activity than the other lysates.

Figure 7:
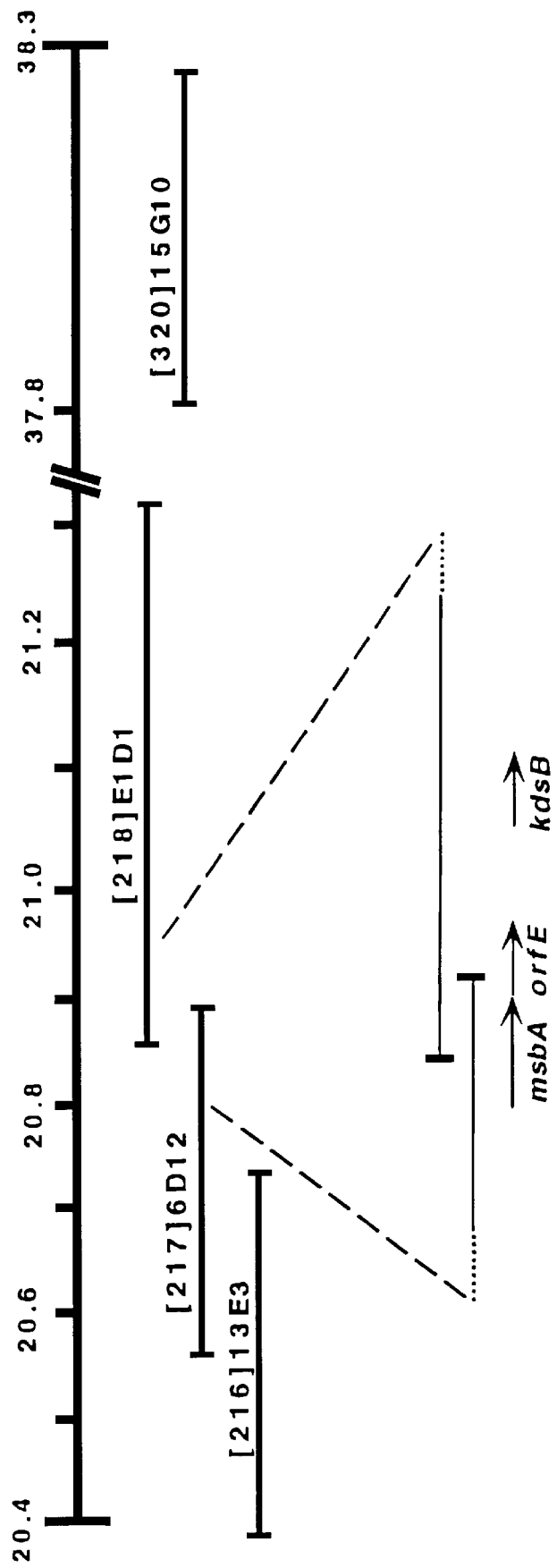
FIG. 7: E. coli DNA contained on Kohara library λ clones used to verify the overexpression of 4' kinase associated with [218]E1D1. The bold bar depicts the relevant E. coli genomic DNA with the minutes designated (Berlyn et al, in Escherichia coli and Salmonella: Cellular and Molecular Biology (Neidhardt, F. C., ed) Vol. 2, Second Ed., pp. 1715–1902, American Society for Microbiology, Washington, D.C. (1996)). Four different Kohara clones, [216]13E3, [217]6D12, [218]E1D1, and [320]15G10, are shown with the genomic DNA included on each. The dashed lines lead to an enlargement of the overlap region between clones [217]6D12 and [218]E1D1. The locations of the msbA, orfE, and kdsB genes are shown.
Figure 8:
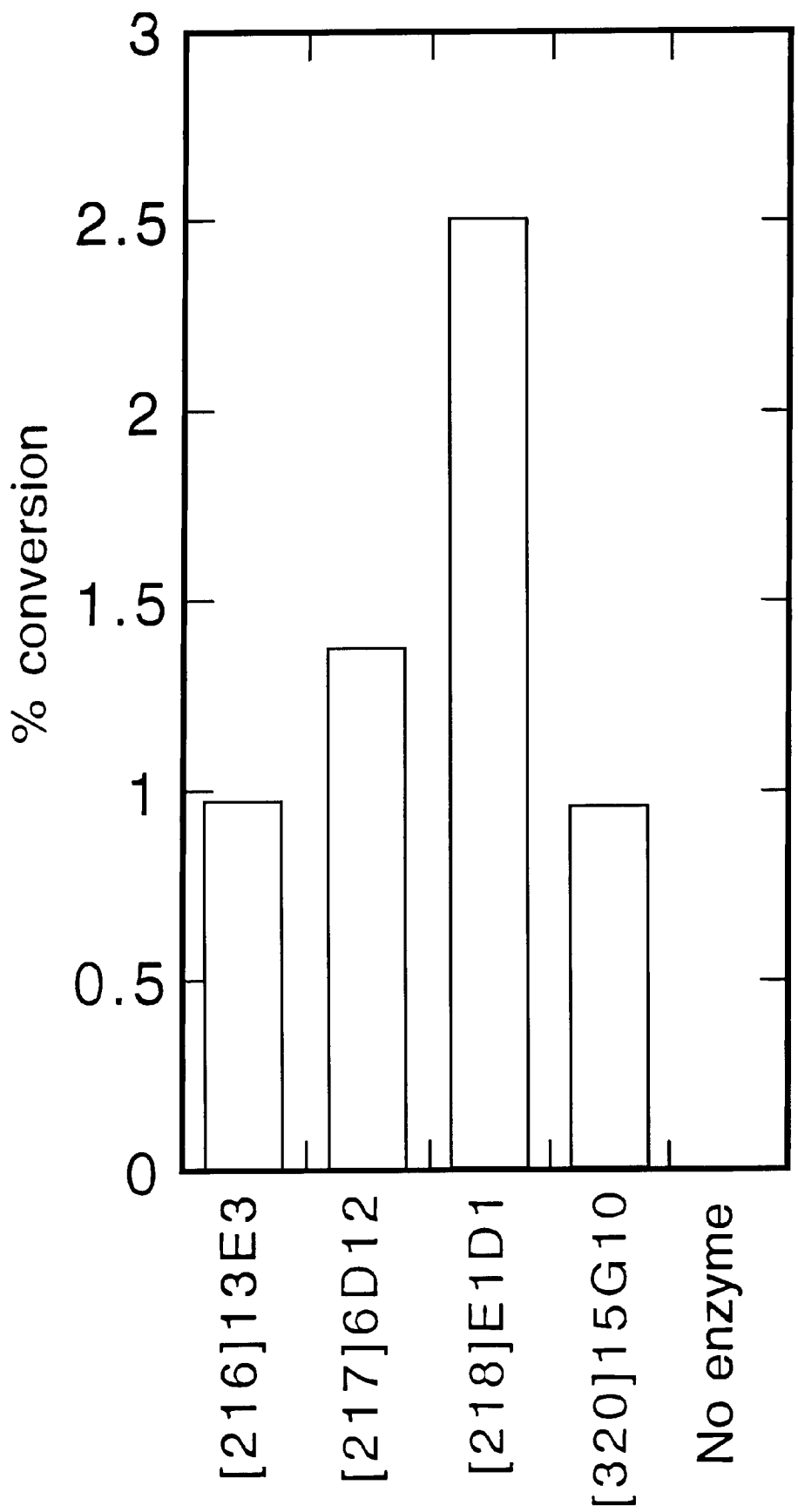
FIG. 8: Re-assay of E. coli lysates generated with selected hybrid λ bacteriophages of the Kohara library for 4' kinase activity. Plaque forming units (pfu) were determined for the lysates made from λ clones [216]13E3, [217]6D12, [218] E1D1, and [320]15G10. Matched lysates were made by infecting E. coli W3110 with 4×10$^{-3}$ pfu as described in the Examples that follow. Lysis occurred 7 to 8 hours after infection. At lysis, the lysates were transferred to fresh tubes and frozen overnight at −80° C. The 4' kinase activity was assayed as described above with reference to FIG. 5. The histogram shows the % conversion of DS-1-$^{32}$P to [1-$^{32}$P]-lipid IV$_A$. The lysate generated with λ clone [218]E1D1 is 2.5 fold more active than the other lysates.

Differences in lysis time could account for some of the variation of the activities seen in the lysates. The original lysates used to make the library were not generated from a fixed titer. To control for this variation among lysates, the plaque forming units (pfu) for lysates derived from λ clones [216]13E3, [217]6D12, and [218]E1D1, and [320]15G10 were determined (FIG. 7). Matched lysates were then made by infecting *E. coli* W3110 with 4×10$^{-3}$ pfu. After 7–8 hours, lysis occurred in each case, and the lysates were again assayed for 4' kinase activity as before. The result is shown in FIG. 8. The lysate of λ[218]E1D1 persisted in having 2–2.5 fold overproduction of 4' kinase activity, compared to controls. This finding led to the further investigation of the genes on λ[218]E1D1.

Figure 5A:
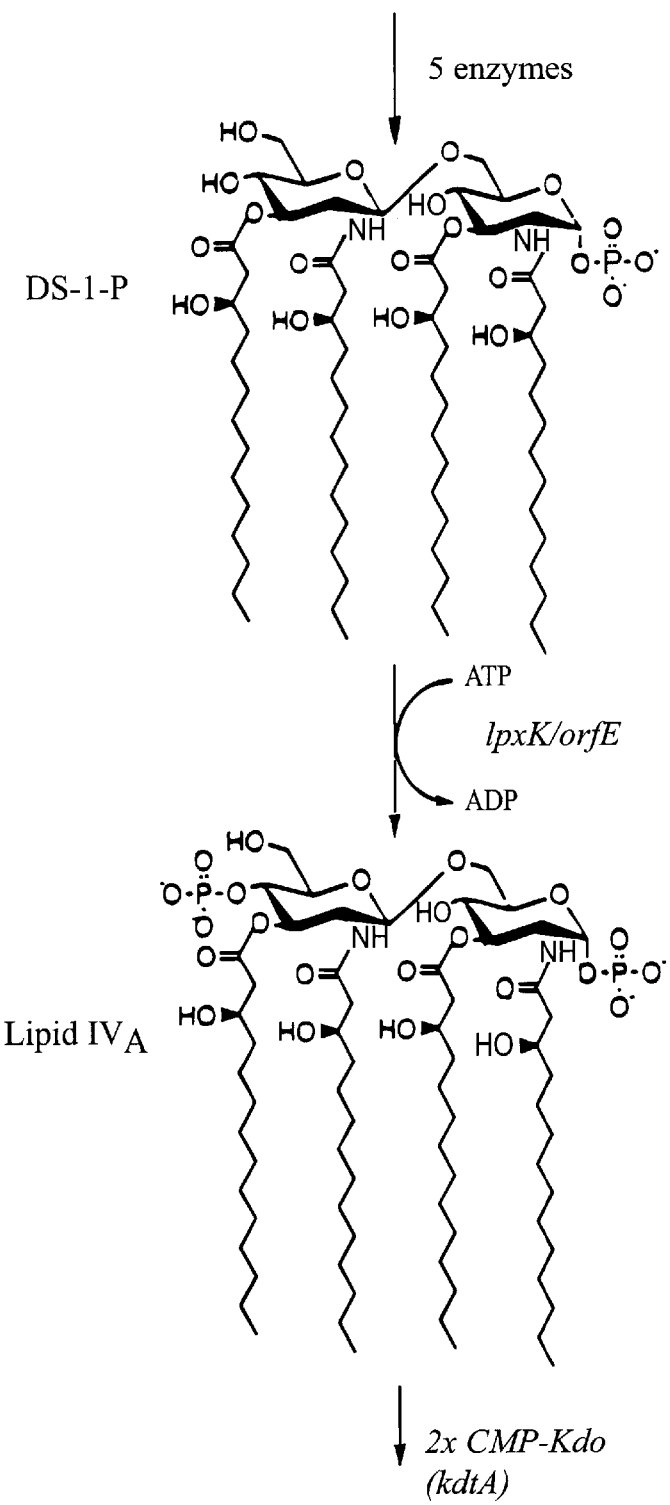
FIGS. 5A and 5B: Biosynthetic pathway for E. coli $Kdo_2$-lipid A. Five enzymes, LpxA, LpxC, LpxD, a UDP-diacylglucosamine pyrophosphatase, and LpxB are required for the synthesis of DS-1-P, the substrate for the 4' kinase. The 4' phosphorylation of DS-1-P yields lipid A. The Kdo transferase, encoded by kdtA, then transfers two Kdo sugars to lipid $IV_A$ to form $Kdo_2$-lipid $IV_A$. The late acyltransferases, HtrB and MsbB, add laurate and myristate, respectively, to form $Kdo_2$-lipid A. $Kdo_2$-lipid A is sufficient to support the growth of E. coli and is fully active as an immunostimulant and as an endotoxin during gram-negative sepsis. Whole cells of mutants lacking MsbB are many orders of magnitude less immunostimulatory than wild type (Somerville Jr. et al, J. Clin. Invest. 97:359–365 (1996)).
Figure 5B:
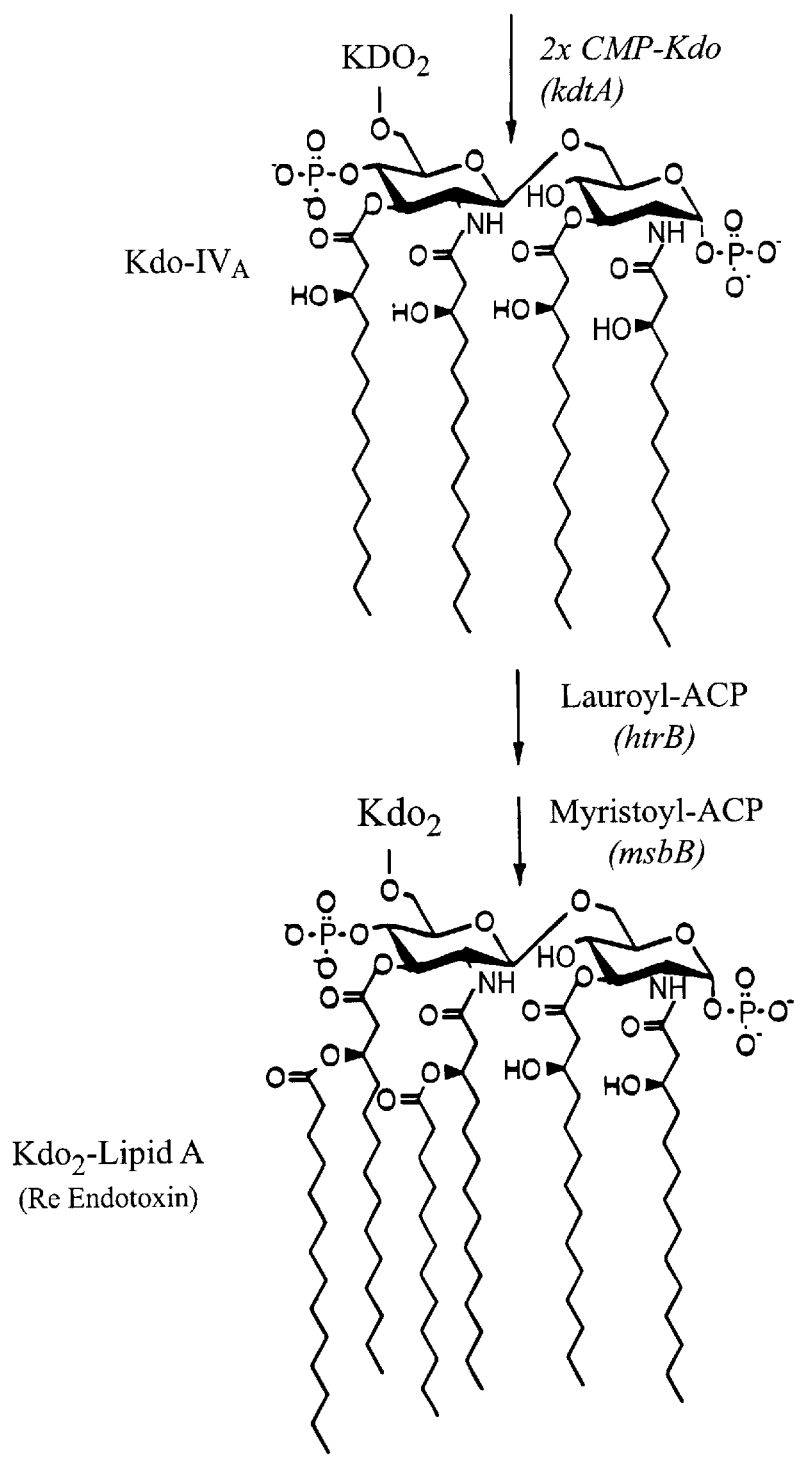

The λ clone [218]E1D1 contains a 20 kb fragment of the *E. coli* genome spanning minutes 20.8–21.3 (Berlyn et al, in *Escherichia coli* and Salmonella: Cellular and Molecular Biology (Neidhardt, F. C., ed) Vol. 2, Second Ed., pp. 1715–1902, American Society for Microbiology, Washington, D.C. (1996)). Two genes in this region, msbA and kdsB, are related to the lipopolysaccharide system. kdsB encodes the CMP-Kdo synthase, and msbA encodes a putative LPS transporter (FIG. 7) with homology to mammalian Mdr proteins. msbA was first identified by Karow and Georgopoulos (Karow et al, Mol. Microbiol. 7:69 (1993), Polissi et al, Mol. Microbiol. 20:1221 (1996)) as a multicopy suppressor of htrB (Karow et al, J. Bacteriol. 173:741 (1991), Karow et al, Mol. Microbiol. 5:2285 (1991), Karow et al, J. Bacteriol. 174:7407 (1992)), the gene encoding the Kdo-dependent lauroyl transferase (FIG. 5). msbA forms an operon with an essential downstream open reading frame, orfE, of unknown function (Karow et al, Mol. Microbiol. 7:69 (1993). Insertion of an Ω chloramphenicol resistance cassette into the msbA gene blocks transcription of both msbA and orfE. Complementation of this msbA/orfE knock-out only occurred with hybrid plasmids encoding both msbA and orfE, supporting the view that both genes are essential. As shown in FIG. 7, only about half of the msbA coding region is on λ clone [218]E1D1. In this clone, orfE is missing its native msbA promoter and expression of this gene would be from readthrough of λ genes. Given the relatively low overproduction of the 4' kinase activity found in lysates generated with [218]E1D1 and the indication that orfE does not have its own endogenous promoter, a plasmid was constructed to overexpress orfE using the T7 RNA polymerase system.

Example II

Massive Over-Expression of 4' Kinase Activity on a Hybrid Plasmid Bearing orfE

Figure 9:
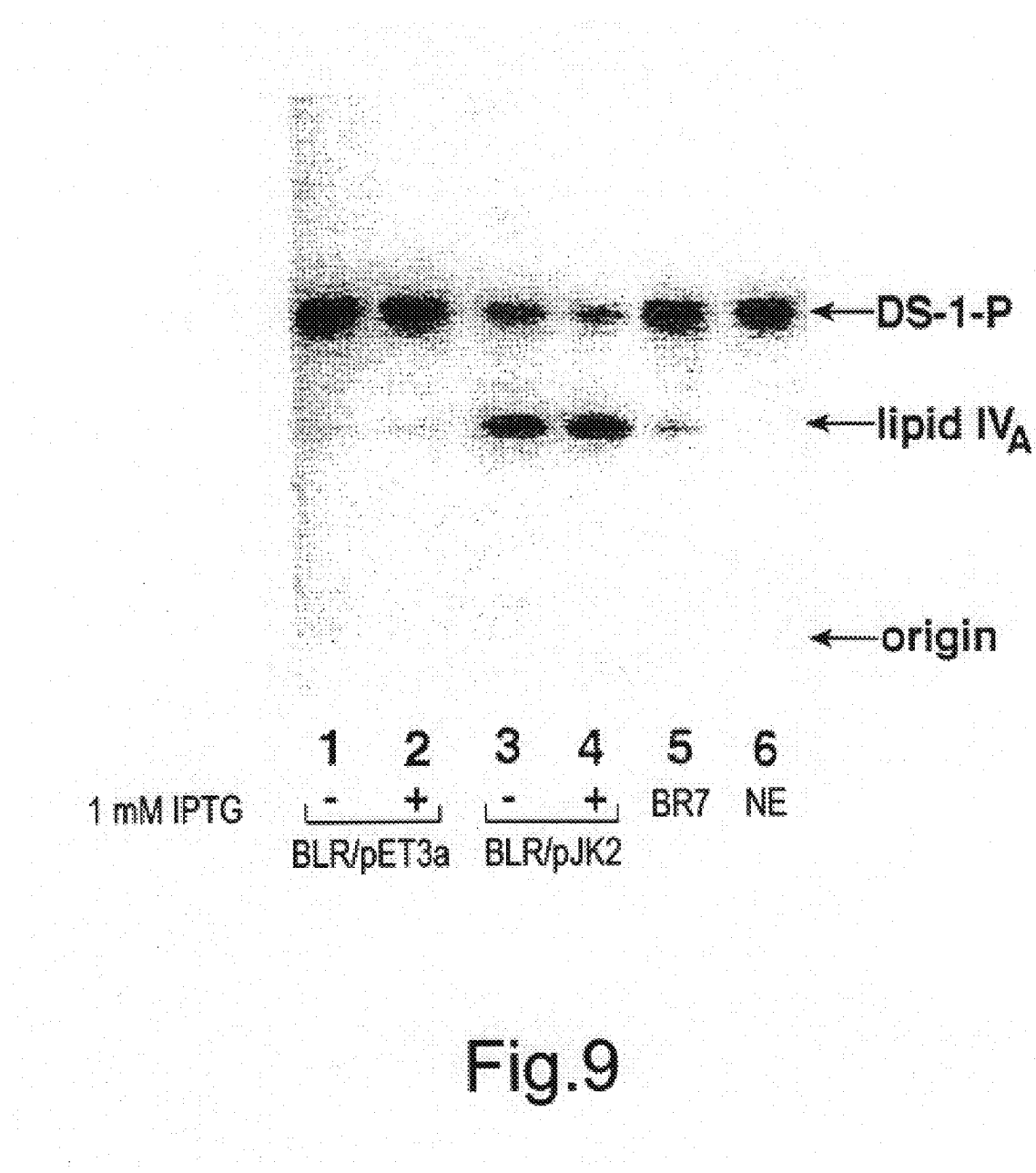
FIG. 9: Massive over-expression of 4' kinase activity on a hybrid plasmid bearing orfE. Washed membranes from BLR(DE3)pLysS/pET3a (lanes 1 and 2), BLR(DE3)pLysS/pJK2 (lanes 3 and 4), and strain BR7 (lane 5) were assayed for 4' kinase activity in a reaction mixture containing 100 μM DS-1-$^{32}$P (1000 cpm/nmol), 1 mg/ml cardiolipin, 50 mM Tris, pH 8.5, 5 mM ATP, 5 mM MgCl$_2$, 1% NP-40, and 0.5 mg/ml washed-membranes. After 10 minutes at 30° C., the reaction was stopped by spotting 5 μl onto Silica Gel 60 TLC plate and developing in chloroform:methanol:water :acetic acid (25:15:4:2, v/v). After chromatography, the plate was dried, exposed to a PhosphorImager screen, and visualized using ImageQuant software. The membranes used in lanes 2 and 4 are from cells that were induced with 1 mM IPTG during the growth of the cells. BLR/pET 3a and BLR/pJK2 are abbreviations for BLR(DE3)pLysS/pET 3a and BLR(DE3)pLysS/pJK2 respectively. NE (lane 6) indicates the no enzyme control. Arrows indicate where the substrate, DS-1-P, and the product, lipid IV$_A$, of the reaction migrate on the TLC plate.

The gene encoding orfE was cloned behind the T7 promoter of pET3a to form pJK2. Plasmid pJK2 was transformed into BLR(DE3)pLysS cells, an *E. coli* strain that carries the T7 RNA polymerase as a λ lysogen (Table I). The expression of T7 RNA polymerase is induced with IPTG and leads to the expression of genes from the T7 promoter. Washed membranes from BR7, an *E. coli* strain deficient for diglyceride kinase (Ray et al, J. Biol. Chem. 262:1122 (1987), Hampton et al, Methods in Enzymology 209:466 (1992)), BLR(DE3)pLysS/pJK2, and BLR(DE3)pLysS/pET3a were assayed for 4' kinase activity using DS-1-$^{32}$P as the phosphate acceptor. The result of this assay is shown in FIG. 9. The 4' kinase activity was highly over-expressed in cells with pJK2 versus strain BR7 or cells with pET3a vector alone (FIG. 9, lanes 3 and 4, versus lanes 1, 2, and 5). When assayed at a protein dilution in which product-formation is linear with respect to time, expression of orfE led to several thousand fold overproduction of 4' kinase activity. Table II shows the specific activities of the 4' kinase in cell-free extracts, membrane free cytosols (subjected to two ultracentrifugations), and washed membranes.

TABLE III

Conversion of DS-[1-$^{32}$P]-lipid IV$_A$ by various fractions of BLR(DE3)pLysS/pET3a and BLR (DE3)pLysS/pJK2

| Strain | Cellular fraction | Specific Activity nmol/min/mg (30° C.) |
|---|---|---|
| BLR(DE3)pLysS/pET3a | cell-free extract | 0.34 |
|  | membranes[1] | 1.75 |
|  | cytosol[2] | ND[3] |
| BLR(DE3)pLysS | cell-free extract | 1.17 × 10$^3$ |
|  | membranes[1] | 3.17 × 10$^3$ |
|  | cytosol[2] | 30.7 |

Figure 10:
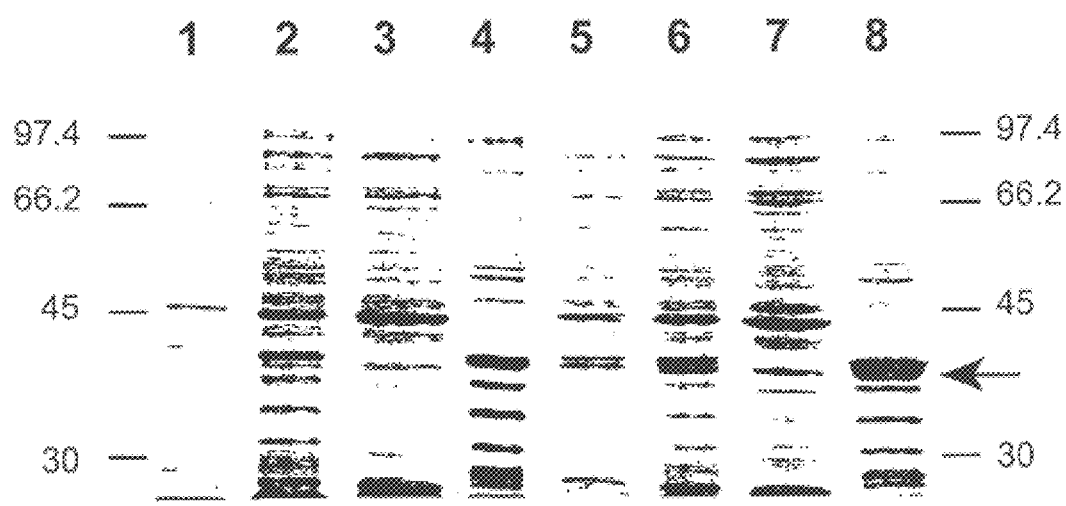
FIG. 10: SDS-polyacrylamide gel analysis of various fractions from wild-type and 4' kinase over-producing strains. Lanes 1–4 are from BLR(DE3)pLysS/pET3a and lanes 5–8 are from BLR(DE3)pLysS/pJK2. Ten μg of protein from whole cells (lanes 1 and 5), cell-free extract (lanes 2 and 6), twice centrifuged cytosol (lanes 3 and 7) and washed membranes (lanes 4 and 8) were subjected to electrophoresis on a 10% SDS-polyacrylamide gel in 1×Laemmli buffer for 45 minutes at 200 V, and then stained with Coomassie Brillant Blue. The migration of the molecular weight standard (in kDa) is indicated on both sides of the gel. The arrow indicates the migration of a protein band specifically elevated in OrfE over-producing extracts. The migration of this band is consistent with the predicted molecular weight of 36 kDa. It is present in whole cells, cell-free extract, and washed membranes of BLR(DE3) pLysS/pJK2 but not in comparable fractions of the same cells harboring vector alone.

[1]Washed membranes were used.
[2]Cytosol subjected to two ultracentrifugations was used.
[3]The activity was too low to measure accurately orfE encodes a 328 amino acid protein with a predicted molecular weight of 36 kDa (Karow et al, Mol. Microbiol. 7:69 (1993)). Analysis of protein fractions from BLR(DE3) pLysS/pJK2 cells by SDS-PAGE shows an over-expressed protein that is not present in protein fractions from BLR (DE3)pLysS/pET3a cells (FIG. 10). The over-expressed protein migrates with the molecular weight predicted from the sequence of orfE and is associated with the membranes (FIG. 10, lane 8). This is consistent with the hydropathy profile of orfE, which predicts 1 or 2 transmembrane helices in the N-terminal region of the protein. Like the protein, the 4' kinase activity is also associated with the membranes consistent with the hypothesis that orfE encodes the enzyme (Table II).

Database searches identified only two open reading frames of unknown function from other gram-negative bacteria with significant homology to orfE. The predicted amino acid sequence of an open reading frame identified in the Haemophilus influenzae Rd genome (Fleischmann et al, Science 269:496 (1995)) is 70.2% similar and 48.4% identical to the predicted amino acid sequence of *E. coli* orfE. The valB gene (Mdluli et al, Microbiology 140:3309 (1994)) from *Francisella novicida* encodes a protein that is 66.8% similar and 41.4% identical to orfE. This strongly suggests that the *H. influenzae* open reading frame and *Francisella*

13

*novicida* valb may also be genes encoding lipid A 4' kinase variants. orfE and its homologues do not display significant sequence similarity to any other type of kinase, including those involved in carbohydrate, lipid, nucleic acid or protein phosphorylation.

Example III

Analysis of Substrate Specificity and Generation of Novel Analogs with the Overproduced Kinase The 4' kinase is a useful tool for making $^{32}$P-labeled substrates for the biochemical analysis of the enzymes catalyzing the late steps of the lipid A pathway (Hampton et al, Methods in Enzymology 209:466 (1992), Brozek et al, J. Biol. Chem. 264:6956 (1989), Brozek et al, J. Biol. Chem. 265:15410 (1990), Clementz et al, J. Biol. Chem. 271:12095 (1996)). $^{32}$P-labeled lipid A precursors and substructures are also useful for studying the interactions of lipid A-like molecules with mammalian cells (Hampton et al, Nature 266:19499 (1991), Hampton et al, Nature 352:342 (1991). To demonstrate the synthetic utility of the overexpressed 4' kinase, several DS-1-P analogs were analyzed as 4' kinase substrates (FIG. 11). DS-1-P is the physiological substrate for the 4' kinase. 3-aza-DS-1-P has an amide-linked hydroxymyristate group at the 3 position instead of an ester-linked group (FIG. 11, NH indicated in bold). Mild alkaline hydrolysis of these compounds results in removal of the ester-linked hydroxymyristate moieties. The structures of the resulting compounds, designated base-treated DS-1-P and base-treated 3-aza-DS-1-P, are also shown.

Figure 12:
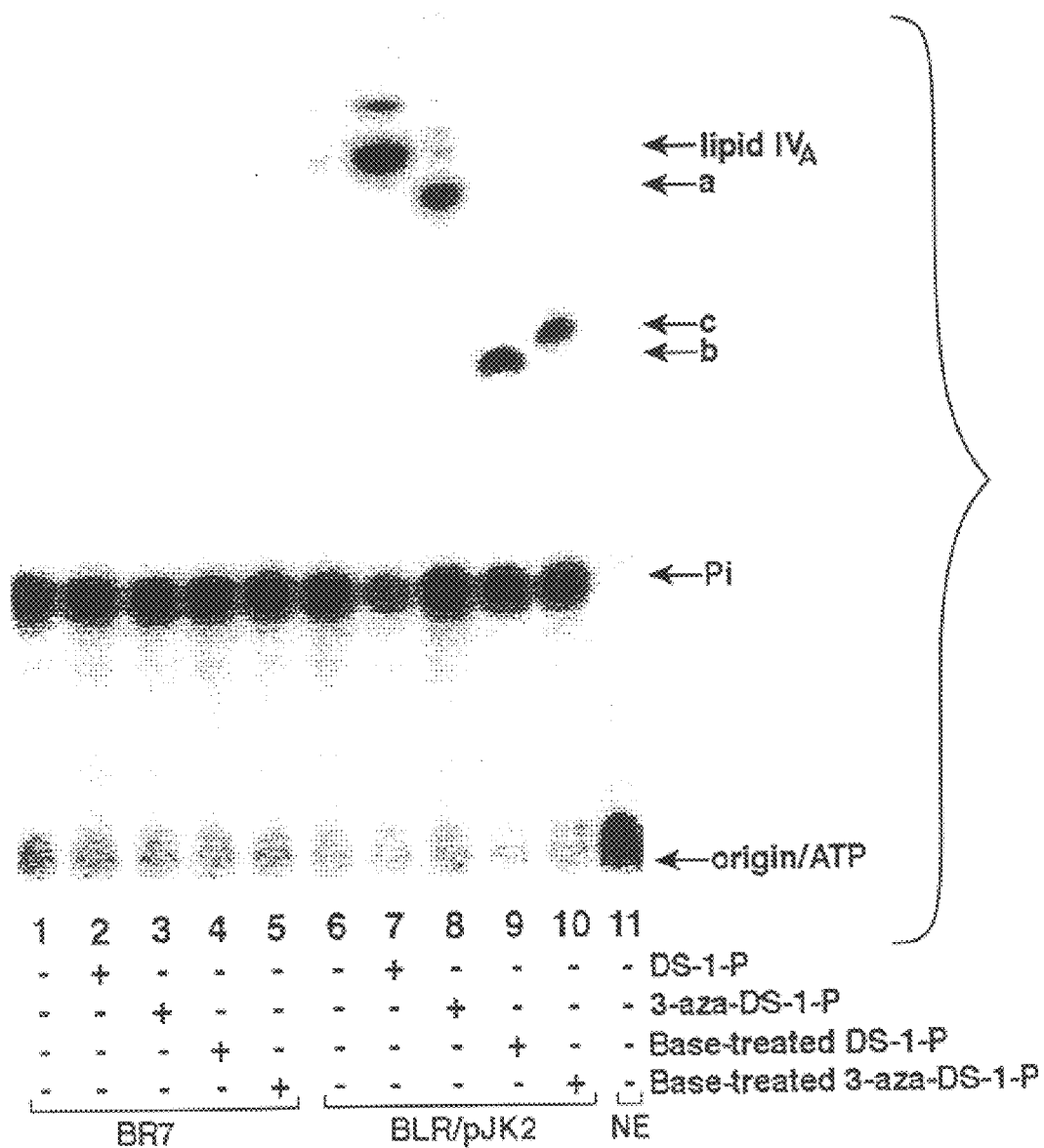
FIG. 12: Effective phosphorylation of DS-1-P and DS-1-P analogs with recombinant, overproduced 4' kinase. Washed membranes from strain BR7 and BLR(DE3)pLysS/pJK2 were used, as indicated, in 4' kinase assays containing 100 μM of the indicated DS-1-P analog, 0.6 μM [γ-$^{32}$P] ATP, 50 mM Tris, pH 8.5, 5 mM MgCl$_2$, 1% NP-40, 1 mg/ml cardiolipin and 0.5 mg/ml washed membranes. After a 10 minute incubation at 30° C., 5 μl of the reaction was spotted onto a Silica Gel 60 TLC plate and developed in chloroform:pyridine:formic acid:water (30:70:16:10 v/v). The plate was dried, exposed to a PhosphorImager screen and visualized using ImageQuant software. Arrows indicate the products of the reactions. If the native substrate DS-1-P is present in the reaction, [4'-$^{32}$P]-lipid IV$_A$ is formed. When 3-aza-DS-1-P, base-treated DS-1-P, or base-treated 3-aza-DS-1-P are present, 4' phosphorylated products a, b and c are formed, respectively. The migration of each of these products is slower than the non-phosphorylated substrate analog, consistent with the phosphate incorporation. As in FIG. 9, BLR/pJK2 is an abbreviation for BLR(DE3)pLysS/pJK2, and NE indicates the no enzyme control. Formation of 4' phosphorylated products is 100–1000 fold more effective with membranes from BLR/pJK2 than with BR7 membranes. Minor $^{32}$P containing lipids generated by membranes of BLR(DE3)pLysS/pJK2 in the absence of any acceptor substrate arise by the action of diglyceride kinase on endogenous glycerophospholipids (see especially Lane 6). The diglyceride kinase is inactivated by mutation in strain BR7 (Hampton et al, Methods in Enzymology 209:466 (1992)).

Each lipid analog was tested as a 4' kinase substrate using recombinant, overexpressed 4' kinase in conjunction with the method II assay conditions (0.6 µM [γ-$^{32}$P]-ATP as the phosphate donor and 100 µM lipid acceptor). DS-1-P becomes phosphorylated to form [4'-$^{32}$P]-lipid IV$_A$ by BR7 membranes (containing wild-type kinase levels), but only with a yield of ~0.5% (FIG. 11, lane 2). When BLR(DE3) pLysS/pJK2 membranes are used (FIG. 12, lane 7) more than 50% of the $^{32}$P is incorporated into [4'-$^{32}$P]-lipid IV$_A$. The 3-aza-DS-1-P, the base-treated DS-1-P, and the base-treated 3-aza-DS-1-P, were also well utilized substrates for the recombinant, over-expressed 4' kinase. Product (a) is formed efficiently from 3-aza-DS-1-P in the presence of BLR(DE3)pLysS/pJK2 membranes, but not BR7 membranes (FIG. 12, lane 8 versus lane 3). Products (b) and (c) are formed from base-treated DS-1-P and base treated 3-aza-DS-1-P, respectively. In each case, the reaction is 100–1000 fold more effective with membranes from BLR(DE3)pLysS/pJK2 membranes than with membranes from BR7 (FIG. 12, lanes 9 and 10 versus lanes 4 and 5).

Example IV

Enzymatic Synthesis of [4'-$^{32}$P]-Lipid A

Figure 13:
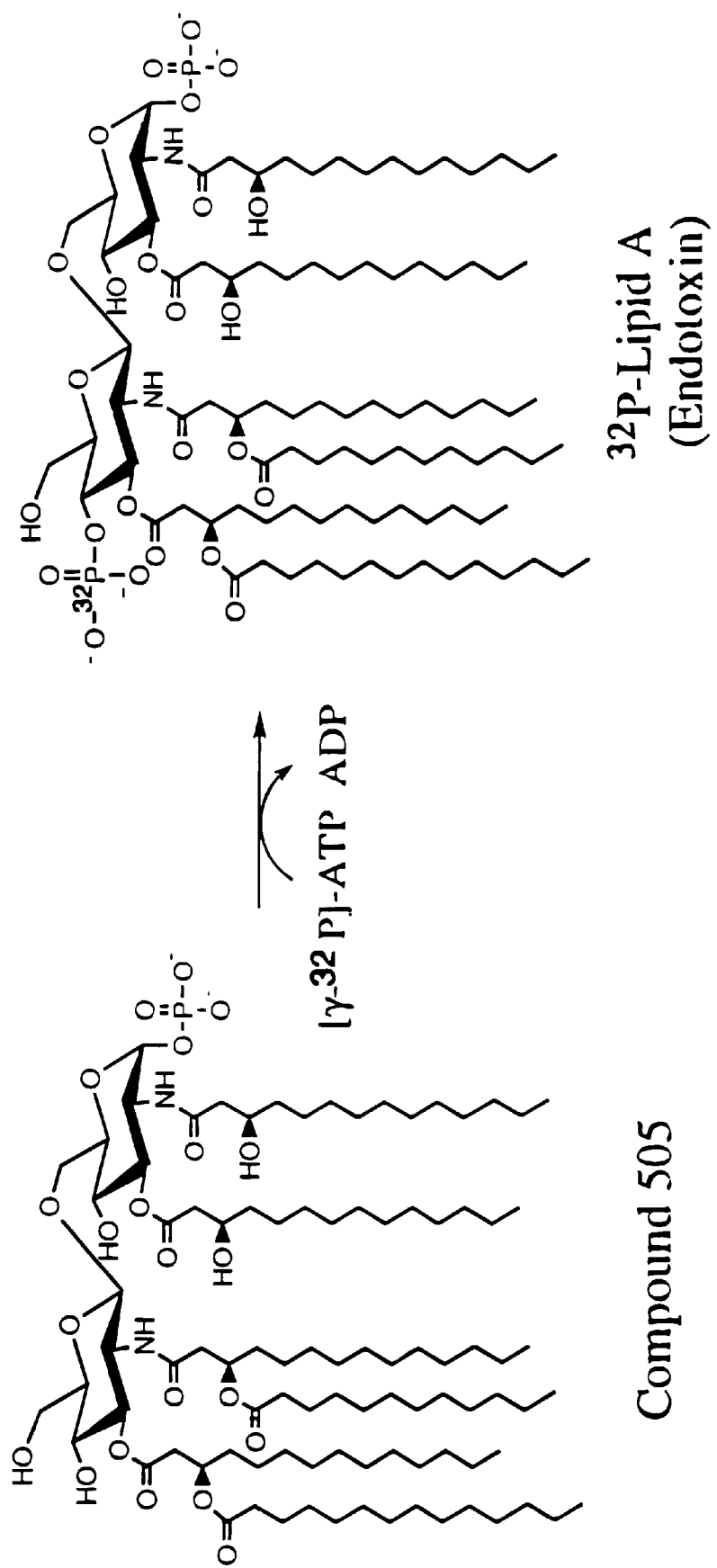
FIG. 13: Proposed reaction catalyzed by the 4' kinase with compound 505 as substrate to form [4'-$^{32}$P]-lipid A. Overexpressed, recombinant 4' kinase is able to catalyze measurable 4' phosphorylation of compound 505 (45–47) to form [4'-$^{32}$P]-lipid A.
Figure 14:
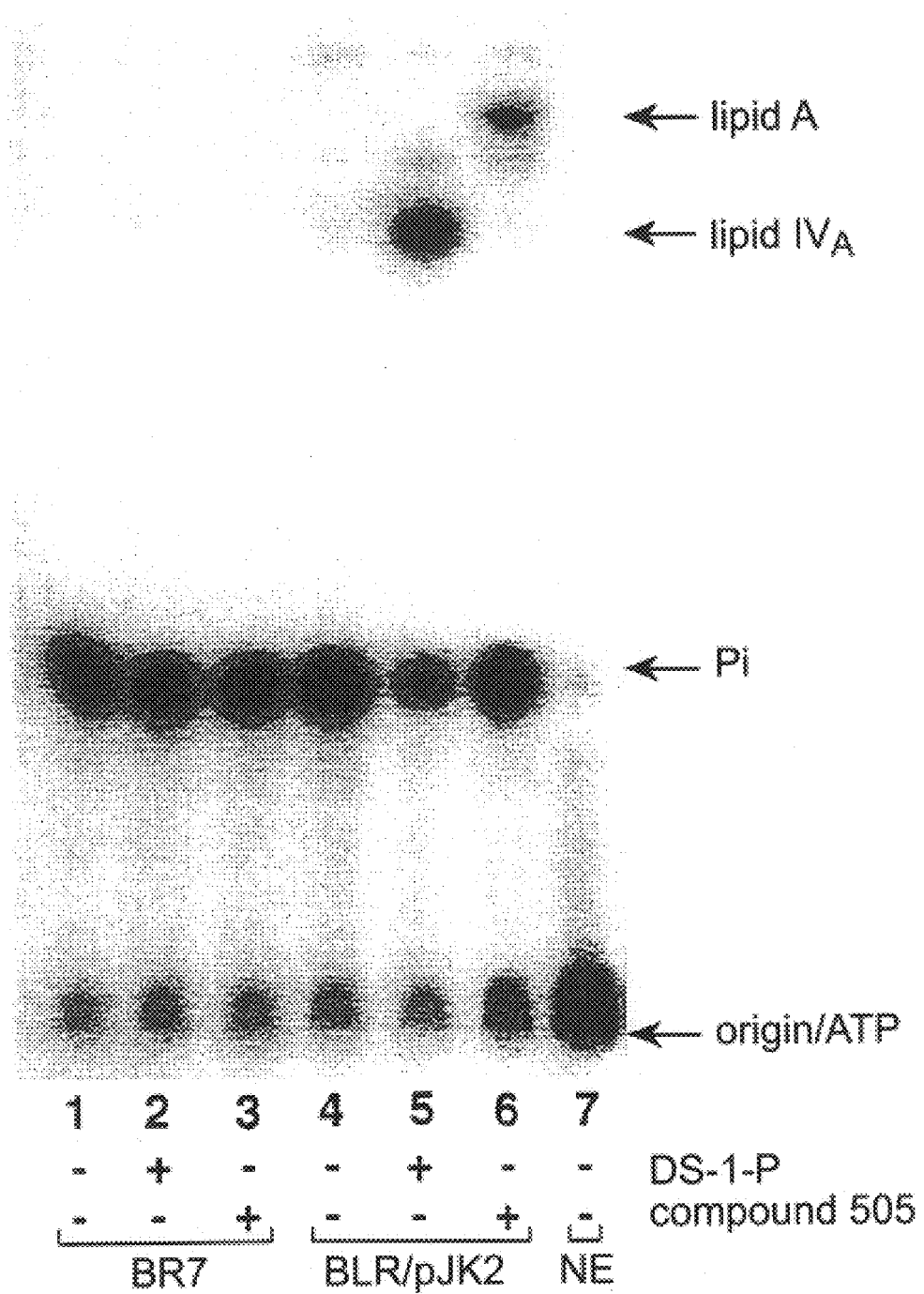
FIG. 14: Generation of [4'-$^{32}$P]-lipid A (endotoxin) from compound 505 using recombinant, overexpressed 4' kinase. Kinase assays were performed exactly as in the legend to FIG. 12, except that DS-1-P and compound 505 were the acceptor lipids used, as indicated. Arrows indicate [4'-$^{32}$P]-lipid IV$_A$, the product when DS-1-P is present, and [4'-$^{32}$P]-lipid A, the product when compound 505 is present. The migration of lipid A formed in this reaction is the same as labeled lipid A isolated after pH 4.5 hydrolysis (Karibian et al, J. Bacteriol 175:2988 (1993)) from wild type cells of E. coli. The yield of the 4'-phosphorylated product represented about 5% of the input [γ-$^{32}$P] ATP when membranes of BLR/pJK2 were employed, but $^{32}$P incorporation was not detectable with BR7 membranes.

The results using the DS-1-P analogs show that the 4' kinase can efficiently phosphorylate disaccharides with 2, 3 or 4 acyl chains. However, some of the most important lipid A-like molecules that display either endotoxin agonist or antagonist activity contain 5 or 6 acyl (or alkyl) chains (Raetz, *Escherichia coli* and Salmonella: Cellular and Molecular Biology (Neidhardt, F. C., ed) Vol. 1, Second Ed., pp. 1035–1063, American Society for Microbiology, Washington, D.C. (1996), Golenbock et al, J. Biol. Chem. 266:19490 (1991), Christ et al, J. Am. Chem. Soc. 116:3637 (1994), Christ et al, Science 265:80 (1995), Takayama et al, Infect. Immun. 57:1336 (1989)). In order to address whether the recombinant, overexpressed 4' kinase would be useful for making $^{32}$P-endotoxin agonists or antagonists, an attempt was made to phosphorylate compound 505, a synthetic hexaacyldisaccharide-1-phosphate (Imoto et al, Bull. Chem. Soc. Jpn. 60:2205 (1987), Loppnow et al, J. Immunol. 142:3229 (1989), Kusumoto et al in Bacterial Endotoxic Lipopolysaccharides, Vol. I: Molecular Biochemistry and Cellular Biology. (Morrison et al, eds), pp. 81–105, CRC Press, Boca Raton (1992)). The 4' phosphorylation of this compound yields the major molecular species that constitutes *E. coli* K-12 lipid A (endotoxin) (Karibian et al, J. Bacteriol. 175:2988 (1993)), as shown in FIG. 13. Compound 505 was tested in a 4' kinase assay system using membranes from BR7 and BLR(DE3)pLysS/pJK2. The results are shown in FIG. 14. When BR7 membranes are used with DS-1-P, a small amount of [4'-$^{32}$P]-lipid IVA product (representing ~0.5% of the input [γ-$^{32}$P]-ATP) is formed (FIG. 14, lane 2). Use of BLR(DE3)pLysS/pJK2 membranes leads to formation of a large amount of lipid IV$_A$ (FIG. 14, lane 5). If compound 505 is assayed with BR7 membranes, no detectable product ([4'-$^{32}$P]-lipid A) was formed (FIG. 14, lane 3). However, with BLR(DE3)pLysS/pJK2 membranes, about 5% of the input $^{32}$P from [γ-$^{32}$P]-ATP is incorporated into [4'-$^{32}$P]-lipid A (FIG. 14, lane 6). The migration of this novel, enzymatically labeled product has the same migration as lipid A isolated by pH 4.5 hydrolysis from wild-type *E. coli* cells. Thus, when greatly over-expressed, the 4' kinase is capable of phosphorylating glucosamine disaccharides that are more or less acylated than the native substrate, DS-1-P. Lipid X and UDP-diacylglucosamine were not substrates for the 4' kinase, even when the enzyme was highly overexpressed. The enzyme apparently has a strong preference for glucosamine disaccharides.

Membranes from *Rhizobium etli* strain CE3, contain an unusual phosphatase that removes the 4' phosphate from the lipid A precursor, KdO$_2$-lipid IV$_A$. Solubilized CE3 membranes were used to make 4' de-phosphorylated KdO$_2$-lipid IV$_A$. The 4' dephosphorylated KdO$_2$-lipid IV$_A$ is not a substrate for the over-expressed 4' kinase. The Kdo disaccharide may interfere with the presentation of the 4'—OH of the glucosamine disaccharide to the kinase.

Example IV

Construction of Plasmids for Generation of lpxK Knockout

The lpxK gene was cloned into pMAK705, a vector with a temperature sensitive origin of replication (Hamilton et al, J. Bacteriol. 171:4617 (1989)). pJK2 and pMAK705 were digested with XbaI and BamHI. The 1 kb lpxK gene from pJK2 and the 6 kb linearized pMAK705 were gel purified from a 1% agarose gel. pMAK705 was dephosphorylated with shrimp alkaline phosphatase (USB). The lpxK gene was ligated into pMAK705. A portion of the ligation mixture was transformed into CaCl$_2$. competent XL1-Blue *E. coli*, and colonies resistant to chloramphenicol were selected. Plasmid DNA was isolated from chloramphenicol resistant clones, and digested with XbaI and BamHI to identify those constructs with the desired insert. This plasmid is called pTAG1. To verify that pTAG1 expressed the lpxK gene using the lac promoter, a cell-free extract was prepared and assayed as indicated above. Extracts of cells containing pTAG1 displayed ~5 fold overexpression of 4' kinase activity versus extracts of cells with vector alone.

A plasmid analogous to pTAG1 was constructed with a kanamycin cassette inserted into the NsiI site of lpxK gene.

pJK2 was digested with NsiI and pUC-4K (Pharmacia) was digested with PstI. The 5.5 kb linearized pJK2 and the 1.2 kb kanamycin cassette from pUC-4K were gel purified and ligated together. A portion of the ligation was transformed into *E. coli* XL1-Blue (Stratagene) and colonies resistant to ampicillin were selected. Plasmids were isolated from ampicillin resistant colonies and digested with NdeI and BamHI to verify the presence of the correct 2.2 kb insert. The lpxK::kan construct described above was digested with XbaI and BamHI and cloned into pMAK705 exactly as for pTAG1, yielding pTAG2.

Construction of Strain TG1/pTAG1,

Mutant with Insertion in Chromosomal Copy of lpxK Covered by Plasmid Bearing lpxK$^+$ and Temperature Sensitive Replicon TG1/pTAG1 was constructed following the method of Hamilton et al. (1989). Competent MC1061 were transformed with pTAG2 and grown at 30° C. to an $A_{600}$ of 0.6. Next, $1 \times 10^5$ cells were plated on prewarmed LB plates containing 30 µg/ml chloramphenicol and incubated at 44° C. This selects for cells in which pTAG2 has integrated into the genome. A single colony was used to inoculate 1 ml LB containing chloramphenicol and grown at 30° C. for 6 hours. This culture was diluted into 100 ml of LB containing chloramphenicol and grown to stationary phase. A portion of the culture was diluted 1:1000 into fresh LB containing chloramphenicol and grown to stationary phase again. The above outgrowth was repeated once more. During this outgrowth, the integrated plasmid will occasionally excise carrying either the wild-type lpxK gene or the lpxK::kan allele (Hamilton et al., J. Bacteriology. 171:4617 (1989)). The cells were plated on LB containing chloramphenicol at 30° C. Cells in which the plasmid had excised were identified by their inability to grow at 44° C. in the presence of chloramphenicol. Plasmids were then isolated from 14 temperature sensitive strains and digested with XbaI and BamHI. Of the 14 colonies, 11 contained the pTAG2 insert. Three, however, had the pTAG1 insert, indicating that the lpxK::kan insertion of pTAG2 had replaced the wild-type lpxK gene on the chromosome (Hamilton et al., J. Bacteriology. 171:4617 (1989)). One of these strains was made recA$^-$ by P1 transduction using BLR(DE3) as the donor. The presence of the recA$^-$-phenotype was verified by the strain's sensitivity to UV light.

This strain (designated TG1/pTAG11) is temperature sensitive for growth, accumulates DS-1-P at the non-permissive temperature and is rescued at 44° C. by the introduction into cells of non-temperature sensitive plasmids bearing lpxK$^+$ of *E. coli* or various lpxK homologs from other bacterial species.

Temperature Sensitivity of TG1/pTAG1

Strain TG1/pTAG1 is a mutant with a kanamycin cassette inserted into the chromosomal copy of orfE/lpxK (orfe is the original gene name, however, given its newly identified function it has been renamed lpxK). This insertion is covered by a plasmid, pTAG1, bearing lpxK+ and a temperature sensitive origin of replication. pTAG1 contains the chloramphenicol resistance gene and cells containing pTAG1 are resistant to chloramphenicol at 30° C. but not at 44° C. At higher temperature the origin of replication on pTAG1 does not function and leads to loss of the plasmid. Strain TG1/pTAG1 was tested for its ability to grow with a chromosomal insertion in the lpxK gene in the absence of pTAG1 by growth at 44° C. A single colony was streaked to two LBV plates containing kanamycin and tetracycline. One plate was incubated at 30° C. and the other at 44° C. TG1/pTAG1 was able to grow and form single colonies at 30° C. but not at 44° C. indicating that the insertional inactivation of lpxK is lethal. This result is consistent with Karow and Georgopolous's finding that orfE was an essential gene (Karow et al, Mol. Microbiol. 7:69 (1993)).

Construction of pTAG6 pNGH1-amp was constructed from pNGH1 (T. Odegaard et al, J. Biol. Chem., submitted). pNGHI was digested with BamHI and SalI yielding 3.9 kb and 1.6 kb fragments. pACYC177 was digested with BamHI and XhoI yielding 2.5 kb and 1.4 kb fragments. The 2.5 kb pACYC177 fragment which contains the β-lactamase gene and 1.6 kb pNGH1 fragment which contains the lac promoter were ligated together to form pNGH1-amp. pJK2 was digested with NdeI and the 5' overhang filled in with Klenow DNA Polymerase (New England Biolabs). The lpxK gene was excised by further digestion with BamHI, yielding a 985 base pair fragment with one blunt end and one BamHI sticky end. pNGH1-amp was digested with SmaI and BamHI. The lpxK fragment was ligated into the digested pNGH1-amp. A portion of the ligation was transformed into XLI-Blue competent cells and colonies resistant to ampicillin were selected. Plasmid DNA was isolated from ampicillin resistant clones and was digested with BamHI and SacI to verify the presence of the correct insert. This plasmid was called pTAG6.

A Complementation Assay for Functional lpxK Genes

A mutant rescue experiment was performed using the *E. coli* lpxK gene to illustrate the use of TG1/pTAG1 for identification of 4' kinase variants. pTAG6 is a plasmid which contains the lpxK gene on a low copy ampicillin resistant vector, pNGH1-amp. Unlike pTAG1, this vector is not temperature sensitive for replication and will be maintained at 44° C. Salt competent TG1/pTAG1 cells were made (Sambrook et al, Molecular Cloning, A laboratory Manual, 2nd Edition), and transformed with pTAG6. Transformed cells were plated on LB plates containing ampicillin and grown overnight at 30° C. Transformants, called TG1/pTAG1/pTAG6, were cured of pTAG1 by growth on plates at 44° C. Unlike strain TG1/pTAG1, TG1/pTAG6 is able to grow and form single colonies at 44° C. TG1/pTAG6 is chloramphenicol sensitive at 30° C. and 44° C. consistent with loss of pTAG1. pTAG6 contains a functional 4' kinase gene and is able to cover the lpxK insertion mutation.

All documents cited above are hereby incorporated in their entirety by reference.

One skilled in the art will appreciate from a reading of this disclosure that various changes in form and detail can be made without departing from the true scope of the invention.

What is claimed is:

1. An isolated nucleic acid consisting of a nucleic acid sequence that encodes an amino acid sequence consisting of SEQ ID NO:4.

2. An isolated nucleic acid consisting of SEQ ID NO:3, or a portion of SEQ ID NO:3 of at least 30 consecutive bases, or the complement of SEQ ID NO:3 or of said portion of at least 30 consecutive bases.

3. The isolated nucleic acid according to claim 2 wherein the nucleic acid consists of SEQ ID NO:3, or said portion of at least 30 consecutive bases.

4. The isolated nucleic acid according to claim 2 wherein said nucleic acid consists of SEQ ID NO:3, or a portion of SEQ ID NO:3 of at least 75 consecutive bases.

5. The isolated nucleic acid according to claim 2 wherein the nucleic acid consists of SEQ ID NO:3.

* * * * *